US009623268B2

(12) United States Patent
Cooke et al.

(10) Patent No.: US 9,623,268 B2
(45) Date of Patent: Apr. 18, 2017

(54) NAIL POLISH

(71) Applicant: Chemence Limited, Corby, Northhamptonshire (GB)

(72) Inventors: Hugh Cooke, Corby (GB); Colin John Brunton, Corby (GB); Maria Dincheva, Corby (GB)

(73) Assignee: Chemence Limited, Northamptonshire (GB)

( * ) Notice: Subject to any disclaimer, the term of this patent is extended or adjusted under 35 U.S.C. 154(b) by 0 days.

(21) Appl. No.: 13/685,422

(22) Filed: Nov. 26, 2012

(65) Prior Publication Data

US 2013/0146077 A1 Jun. 13, 2013

Related U.S. Application Data

(60) Provisional application No. 61/564,573, filed on Nov. 29, 2011, provisional application No. 61/601,457, filed on Feb. 21, 2012.

(30) Foreign Application Priority Data

Nov. 24, 2011 (GB) .................................. 1120334.6

(51) Int. Cl.
*A61K 8/37* (2006.01)
*A61Q 3/02* (2006.01)
*A61K 8/46* (2006.01)
*A61K 8/81* (2006.01)
*A61K 8/85* (2006.01)
*A61K 8/87* (2006.01)
*C09D 4/06* (2006.01)
*C08F 222/10* (2006.01)

(52) U.S. Cl.
CPC .................. *A61Q 3/02* (2013.01); *A61K 8/37* (2013.01); *A61K 8/46* (2013.01); *A61K 8/8152* (2013.01); *A61K 8/85* (2013.01); *A61K 8/87* (2013.01); *C09D 4/06* (2013.01); *A61K 2800/81* (2013.01); *C08F 222/1006* (2013.01)

(58) Field of Classification Search
None
See application file for complete search history.

(56) References Cited

U.S. PATENT DOCUMENTS

| | | | |
|---|---|---|---|
| 3,896,014 A | 7/1975 | Rosenberg | |
| 3,928,113 A | 12/1975 | Rosenberg | |
| 4,234,676 A | 11/1980 | Hein et al. | |
| 5,922,334 A | 7/1999 | Krasnansky et al. | |
| 6,803,394 B2 * | 10/2004 | Lilley et al. | 522/182 |
| 2003/0073753 A1 | 4/2003 | Lilley et al. | |
| 2007/0010617 A1 | 1/2007 | Ishikawa et al. | |
| 2011/0256079 A1 | 10/2011 | Kozachek | |

FOREIGN PATENT DOCUMENTS

| | | |
|---|---|---|
| GB | 2234976 A | 2/1991 |
| GB | 2 452 566 A | 3/2009 |
| JP | 50-19941 | 3/1975 |
| JP | 2011020956 | 2/2011 |

OTHER PUBLICATIONS

Hoyle, et al., "Thiol-Enes: Chemistry of the Past with Promise for the Future", Journal of Polymer Science: Part A Polymer Chemistry, 42: 5301-5338 (2004).
European Patent Office Examination Report, dated Sep. 21, 2016, in corresponding European Application, No. EP 12791844.9, filed Nov. 26, 2012.
Japanese Examination Report, English translation, dated Dec. 13, 2016 issued in corresponding Japanese application No. 2014-542937.

* cited by examiner

*Primary Examiner* — Tigabu Kassa

(57) ABSTRACT

This invention relates to nail coating compositions, to packages including the nail coating compositions, to methods of applying the nail coating composition to a nail and to a use of an additive compound to improve the properties of the nail coating composition of the present invention. In particular, the invention relates to nail coating compositions having improved chip resistance, good adhesion to the nail, a high gloss finish and a short dry-to-touch time.

45 Claims, No Drawings

NAIL POLISH

CROSS-REFERENCE TO RELATED APPLICATIONS

This application claims the benefit of GB 1120334.6 filed on Nov. 24, 2011; U.S. Provisional Pat. App. No. 61/564,573, filed Nov. 29, 2011; and U.S. Provisional Pat. App. No. 61/601,457, filed Feb. 21, 2012, each of which is incorporated by reference in its entirety for all purposes.

This invention relates to novel nail coating compositions, to packages including the novel nail coating compositions, to methods of applying the nail coating composition of the present invention and to a use of an additive compound to improve the properties of the nail coating composition of the present invention. In particular, the invention relates to novel nail coating compositions having improved chip resistance, good adhesion to the nail, a high gloss finish and a short dry-to-touch time.

BACKGROUND

Nails have been decorated for a very long time. The staining of nails with henna has been traced back to the Ancient Egyptians.

Nowadays, the decoration and colouration of fingernails, toenails and artificial nail extensions rely, almost exclusively, on a number of well-established techniques: (1) applying a polymer based, pigmented nail lacquer in a solvent or solvents by a coating process and then subsequently evaporating the solvent or solvents; (2) mixing, applying and thermally curing two part (liquid and powder) acrylic components; and (3) applying by a coating process ethylenically unsaturated, UV radiation curable gels or top coats and subsequently curing the coating under a low intensity ultraviolet light source.

Most nail coatings are based on formulations that comprise a solvent and a film former (mentioned as (1) above). Although there has been some variation with the choice of solvent in the nail coating composition, the general components of modern nail coatings are very similar to those invented 80 years ago. There are only a small number of nail coatings manufacturers throughout the World, which might explain the stagnation in this particular field. Thus, modern nail coatings are essentially solvent borne films containing nitrocellulose, pigments, dyes and other optimizing substances.

The solvents most favoured in conventional nail coating compositions are polar organic ester and alcohol solvents for example butyl acetate, ethyl acetate and isopropanol. Toluene is still used in some countries, but because of its carcinogenicity, toluene is being phased out. These particular solvents have been chosen largely because of their ability to evaporate quickly and therefore allow the nail coating composition to dry quickly. Of course, nowadays there is a drive to improve the environmental-friendliness of products. A significant proportion of the content of conventional nail coating composition is solvent, which is evaporated when the nail coating composition is applied. This portion of the nail coating composition is therefore wasted. Additionally, the presence of the solvent in the nail coating composition leads to unnecessary weight in the transportation of the product to its point of sale.

In light of the introduction of regulations to reduce the use of volatile solvents in products, there have been attempts to reduce the usage of volatile solvents in nail coating compositions. For example, there have been attempts at using a water-based acrylic polymer emulsion. However, water-based compositions dry too slowly to be commercially viable.

UK Patent Application No. GB 2 452 566 is an earlier filed patent application of the same applicant. This document discloses a nail coating composition comprising a radiation curable nail coating substance and at least one dye and/or pigment dissolved and/or dispersed in the composition to impart a colour to the coating. The composition disclosed in this document does not use a volatile solvent in the composition, but instead uses an oil to disperse the pigment. The single example provided in this document is a radiation curable substance that comprises a thiol compound in an amount of about 2% w/w of the composition.

A study on these compositions suggested that the coating that resulted from the application and subsequent curing of this composition to the nail for 2 to 5 minutes was indistinguishable in appearance from that of a nail coated with a conventional solvent-based lacquer (when dried for a longer period of time).

Although the composition disclosed in the example of GB 2 452 566 exhibits an excellent thermal stability, resistance to premature cross-linking (i.e. cross-linking when in the bottle) and polymerisation and excellent shelf life properties, this product is rendered not commercially viable on account of its poor durability. Unfortunately, this document does not address important issue that the nail composition does not have an adequate level of chip resistance. Subsequent tests demonstrated that nail coating is prone to chipping after only two days. Thus, the adhesion of the coating produced by the composition of GB 2 452 566 is unsatisfactory in that the coating may become detached from the nail too quickly.

Thus, another desirable property of a nail coating composition is a high chip resistance once cured.

An article by Hoyle et al, Journal of Polymer Science; Part A; Polymer Chemistry; Vol. 42, 5301-5338 (2004) discloses that the photo polymerization of mixtures of multifunctional thiols and alkenes is an efficient method for the rapid production of films and thermoset plastics. It is disclosed that one of the major obstacles in traditional free radical photo polymerization is essentially eliminated in thiol-ene polymerizations because the polymerization occurs in air almost as rapidly as in an inert atmosphere.

This review article explains that general, thiol-ene systems polymerize by a free-radical chain mechanism involving two steps: an initial addition of the thiyl radical to the carbon of an ene functionality and a subsequent hydrogen abstraction of a thiol group by a carbon-centred radical to give a thiyl radical. Termination occurs by radical-radical coupling. The two-step process in results in the addition of a thiol group across an ene double bond:

Initiation

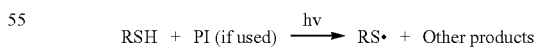

Progagation 1

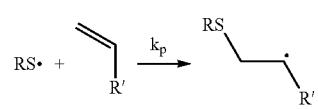

Propagation 2

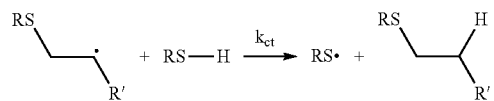

Termination

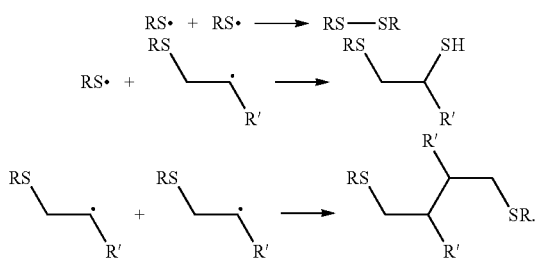

It is also disclosed in this document that, although almost any type of alkene can participate in the reaction, methacrylate compounds are the slowest to react with the thiol component because of their relatively poor reactivity.

In order to improve chip resistance, conventional UV curable nail coatings utilise a multi-step/multi-product system. Thus, many nail coating systems require the application of several products in sequence to achieve the desired chip resistance. A UV curable undercoat treatment may first be applied to the nail to achieve a high degree of adhesion to the nail itself. Then a UV curable colour coating is applied in one or two layers to decorate the nail in a particular colour. Finally, a UV curable top coat of extremely glossy finish may be applied. Of course, the various products required for this system make the whole process a costly and laborious exercise. Further, mild abrasion may be required to remove the various UV cured nail coatings.

Alternatively, to achieve merely a transparent lightly coloured or glitter coating effect, UV curable coatings are often applied alone and then cured as in (3) above.

A problem with the use of UV curable compositions (mentioned as (3) above) is that UV curable compositions are inhibited from curing by air at the top surface of the coating. This means that to achieve a very high gloss and non tacky surface finish an additional subsequent process involving wiping away traces of incompletely cured material with a solvent soaked cloth or pad is also required.

US2003/0073753 discloses a composition for actinic radiation curable nail coatings and artificial nail tips comprising a BISGMA based urethane resin, an additional polymer, a photoinitiator and having a viscosity of greater than approximately 80,000 cps. There is also disclosed a single composition having 11.11% w/w of a specific tri-functional thiol in the composition. It is disclosed that the composition including the tri-functional thiol is "more tack-free" and that the coating is less brittle than when the composition does not include the thiol. However, the composition of this document does not demonstrate the desired properties that the coating is a dry-to-touch coating, i.e. a coating that, when applied to the nail and exposed to UV radiation, is entirely tack-free and does not require any wiping to remove the tacky outer layer that has not cured. Indeed subsequent testing by the applicant confirms that compositions having this level of thiol do not demonstrate the desired properties of an entirely tack-free, dry to touch composition, see Example 15 which includes a composition having 11.0% of a trifunctional thiol. The compositions of the present invention demonstrate the desirable properties of being entirely tack-free and dry-to-touch without the need to wipe off the tacky outer layer that has not cured and therefore represent a novel and inventive improvement over these prior art compositions.

US2007/0010617 discloses an aqueous dispersion for nail enamel. The aqueous dispersion includes a copolymer which is manufactured using an acrylate monomer and another radical-polymerisation unsaturated monomer in the presence of a thiol component. The actual nail enamel does not itself include a thiol component; the thiol component is utilised in the manufacture of the copolymer, and the copolymer is part of the aqueous dispersion for nail enamel. The copolymer that is produced is in the form of an aqueous dispersion which is then mixed with pigments and monomers to provide an aqueous nail enamel composition. Furthermore, although it is mentioned that the copolymer that is used in the aqueous dispersion for nail enamel can be manufactured using a thiol component having a formula of $(HS-CH_2-CH_2-COO)_n-R$, wherein n can be 1 to 4, the examples only recite the manufacture of the copolymer using mono-functional thiol components; bis-, tris- and tetra-functional thiol components are not recited in the examples of US2007/0010617. In fact, the purpose of the thiol component is to chain-terminate the polymer with the thiol group and thus to control the emulsion polymerisation of the methacrylated monomers. The single thiol group will attach itself to the end of the chain by donating a hydrogen atom from the SH group and stop chain propagation at that end. Accordingly, the thiol component that is utilised in the manufacture of the copolymer can only be a mono-functional thiol as higher functional thiol components would be too reactive with the other acrylate monomer and radical-polymerisation unsaturated monomer components. Furthermore, there are always 10 parts or less thiol in the compositions of US2007/0010617, which means that the thiol component will always completely react with the methacrylate and unsaturated monomer components in the composition. Accordingly, the copolymer manufactured will never include a free —SH group for further reaction in the aqueous dispersion of the nail enamel.

U.S. Pat. No. 5,922,334 discloses a nail composition having a thiol component as a chain transfer agent. The chain transfer agent is used at a level from about 0.01 to 5 weight percent based on the total weight of the monomer. Examples of chain transfer agents include 3-mercaptopropionic acid and t-dodecyl mercaptan, i.e. thiol components having a single —SH group. There is no disclosure of thiol components having two or more —SH groups.

U.S. Pat. No. 3,896,014 discloses the use of an allyl oligomer in conjunction with a polythiol in a UV curable nail coating. However, the compositions in this document are based solely on polyenes, thiols and photoinitiators (i.e. the compositions do not include a monomer component). This means that the cured coatings will cross link very strongly and will be very difficult, if not impossible, to remove by a solvent soak off process if applied directly to the nail. The authors of U.S. Pat. No. 3,896,014 recommend the use of a tie coat layer with water swellable properties so that the complete nail coating can be removed in warm water. Thus, in order to obtain removal in warm water it is essential to apply the water soluble base coat. It is mentioned in U.S. Pat. No. 3,896,014 that the coating can be applied with or without a tie coat layer. However, there are problems when a tie coat is not used. If a tie coat layer is not used, the adhesion to the nail is poor (it will only last 12-24 hours before chipping occurs) and the only described method of removing the nail coating is to remove it by chipping (soaking off the nail coating is not an option). Accordingly, the only practical application of the UV curable nail coatings of U.S. Pat. No. 3,896,014 is to utilise a tie coat, which is time consuming and more costly.

In summary, therefore, the desired properties from a nail coating are:
good adhesion to the nail;
good impact resistance so that it does not chip off easily;
short drying time with a dry to touch surface finish;
high gloss shiny surface;
good compatibility with a vast array of conventional colorants; and
readily removable by the use of traditional nail polish removers.

Objects of the Invention:

It is an aim of the present invention to provide a nail coating composition having good adhesion to the nail itself. It is therefore an aim of the present invention to provide a nail coating composition having a high chip resistance. It is therefore an aim of the present invention to provide a nail coating composition having a chip resistance of at least two days, preferably at least three days, preferably at least five days and more preferably at least ten days.

It is also an aim of the present invention to provide a nail coating composition having a short dry-to-touch time. It is therefore an aim of the present invention to provide a nail coating composition having a dry-to-touch time of 5 minutes or less, preferably 3 minutes or less and more preferably 2 minutes or less, e.g. no longer than 1 minute.

It is also an aim of the present invention to provide a nail coating composition having a high gloss finish.

It is also an aim of the present invention to provide a nail coating composition which may be applied to a nail in a single step (i.e. without the need for an undercoat or a top coat).

It is also an aim of the present invention to provide a nail coating composition which is compatible with most conventional colorants.

It is also an aim of the present invention to provide a nail coating composition which can be removed from the nail using conventional nail polish removers (i.e. without the need for abrasion).

It is also an aim of the present invention to provide a nail coating composition which avoids the use of volatile solvents.

The present invention achieves one or more, e.g. all, of the above listed aims.

BRIEF SUMMARY OF THE DISCLOSURE

In accordance with the present invention there is provided a nail coating composition comprising: a radiation curable composition; and a thiol compound present in an amount of from about 5% to about 90% w/w of the nail coating composition.

In accordance with the present invention there is provided a package comprising: (i) a nail coating composition comprising: a radiation curable component comprising an acrylate-terminated oligomer in combination with at least one acrylate monomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition; and (ii) a means for applying the nail coating composition to a nail.

In accordance with the present invention there is provided a package comprising: (i) a nail coating composition comprising: a radiation curable component comprising an acrylate-terminated oligomer in combination with at least one acrylate monomer; or an allyl-terminated oligomer in combination with at least one acrylate monomer and at least one acrylate-terminated oligomer; or an allyl-terminated oligomer in combination with at least one acrylate monomer or at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition; and (ii) a means for applying the nail coating composition to a nail.

In accordance with the present invention there is provided a package comprising: (i) a nail coating composition comprising: a radiation curable component comprising an allyl-terminated oligomer in combination with at least one acrylate monomer and at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition; and (ii) a means for applying the nail coating composition to a nail.

In accordance with the present invention there is provided a package comprising: (i) a nail coating composition comprising: a radiation curable component comprising an allyl-terminated oligomer in combination with at least one acrylate monomer or at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition; and (ii) a means for applying the nail coating composition to a nail.

In accordance with the present invention there is provided a package comprising: (i) a nail coating composition comprising: a radiation curable component comprising an allyl-terminated oligomer in combination with at least one acrylate monomer and/or at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition; and (ii) a means for applying the nail coating composition to a nail.

In accordance with the present invention there is provided a nail coating composition comprising: a radiation curable component comprising an acrylate-terminated oligomer in combination with at least one acrylate monomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition.

In accordance with the present invention there is provided a nail coating composition comprising: a radiation curable component comprising an allyl-terminated oligomer in combination with at least one acrylate monomer and/or at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition.

In accordance with the present invention there is provided a package comprising: (i) a nail coating composition comprising: a radiation curable component comprising an acrylate-terminated oligomer in combination with at least one acrylate monomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition and when the thiol consists of a tetra or higher functional thiol it is present as at least 10% of the nail coating composition; and (ii) a means for applying the nail coating composition to a nail.

In accordance with the present invention there is provided a package comprising: (i) a nail coating composition comprising: a radiation curable component comprising an allyl-terminated oligomer in combination with at least one acrylate monomer and/or at least one acrylate-terminated oligomer; and a thiol component present in an amount of from about 5% to about 90% w/w of the nail coating composition, wherein the thiol component comprises a compound containing two or more SH groups, and wherein when the thiol component consists of a bis and/or tris functional thiol it is present as at least 15% of the nail coating composition and when the thiol consists of a tetra or higher functional thiol it is present as at least 10% of the nail coating composition; and (ii) a means for applying the nail coating composition to a nail.

In accordance with the present invention there is provided a nail coating composition comprising: a radiation curable component comprising an acrylate-terminated oligomer in combination with at least one acrylate monomer; and a thiol component present in an amount of from about 5% to about 90% w/w of the nail coating composition, wherein the thiol component comprises a thiol compound containing two or more SH groups, and wherein when the thiol component consists of a bis and/or tris functional thiol it is present as at least 15% of the nail coating composition and when the thiol consists of a tetra or higher functional thiol it is present as at least 10% of the nail coating composition.

In accordance with the present invention there is provided a nail coating composition comprising: a radiation curable component comprising an allyl-terminated oligomer in combination with at least one acrylate monomer and/or at least one acrylate-terminated oligomer; and a thiol component present in an amount of from about 5% to about 90% w/w of the nail coating composition, wherein the thiol component comprises a thiol compound containing two or more SH groups, and wherein when the thiol component consists of a bis and/or tris functional thiol it is present as at least 15% of the nail coating composition and when the thiol consists of a tetra or higher functional thiol it is present as at least 10% of the nail coating composition.

In accordance with the present invention there is provided a radiation curable nail coating composition which cures to directly form a dry to touch nail coating.

In accordance with the present invention there is provided a method of applying the nail composition of the present invention to a nail, the method comprising: contacting the nail with the composition; and exposing the composition to radiation to cure the composition.

In accordance with the present invention there is provided a method of applying the nail composition of the present invention to a nail, the method comprising: directly contacting the nail with the composition; and exposing the composition to radiation to cure the composition.

In accordance with the present invention there is provided a method of applying the nail composition of the present invention to a nail, the method comprising: contacting the nail with the composition; and exposing the composition to radiation to cure the composition; wherein the method does not include a step of wiping off an uncured outer layer of the nail composition.

In accordance with the present invention there is provided a use of a thiol compound in a nail composition, the nail composition comprising a radiation curable component and a thiol compound present in an amount of from about 5% to about 90% w/w of the nail coating composition, for improving the adhesion of the nail coating composition to the nail.

In accordance with the present invention there is provided a use of a thiol compound in a nail composition, the nail composition comprising a radiation curable component and a thiol compound present in an amount of from about 5% to about 90% w/w of the nail coating composition, for increasing the chip resistance of the nail coating composition.

In accordance with the present invention there is provided a use of a thiol compound in a nail composition, the nail composition comprising a radiation curable component and a thiol compound present in an amount of from about 5% to about 90% w/w of the nail coating composition, to impart the beneficial dry-to-touch and high gloss characteristics of the nail coating composition.

In accordance with the present invention there is provided a use of a thiol compound in a nail composition of the invention for improving the adhesion of the nail coating composition to the nail.

In accordance with the present invention there is provided a use of a thiol compound in a nail composition of the invention for increasing the chip resistance of the nail coating composition.

DETAILED DESCRIPTION

Definitions:

For the avoidance of doubt, it is hereby stated that the information disclosed earlier in this specification under the heading "Background" is relevant to the invention and is to be read as part of the disclosure of the invention.

The term "nail" includes both natural nails and also artificial and false nails.

As described herein, the nail composition may include a number of components. The sum of the percentage contents of the components of the nail composition equals 100%. For example, the composition may be described as comprising from about 5% to about 90% w/w of a thiol and from about 5% to about 90% w/w of an acrylic acid-terminated oligomer. Thus, by way of example only, the composition may have 50% w/w of a thiol compound. In this case, the remaining 50% w/w of the composition may be the acrylic acid-terminated oligomer and photoinitiator. The nail coating composition may include one or more additional components selected from photoinitiator(s), thickening agent(s), free-radical stabiliser(s), colorant(s), chelator(s) and adhesion promoter(s) amongst others. Unless otherwise stated, all percentages herein refer to percentage weight based on the total weight of the composition concerned.

For convenience, carbon atom ranges disclosed in this specification are defined by reference to the end points of the range. However, all intermediate carbon atom numbers of any specifically mentioned range are also disclosed. Thus, $C_{1-10}$ means a moiety having 1, 2, 3, 4, 5, 6, 7, 8, 9 or 10 carbon atoms, $C_{1-4}$ means a moiety having 1, 2, 3 or 4 carbon atoms and $C_{3-6}$ means a moiety having 3, 4, 5 or 6 carbon atoms.

The term "each independently selected from the group comprising" or "each independently selected from the group consisting of" means that each of the listed 'R' groups may be selected independently of the other 'R' groups (here the term 'R' group refers to any group R, $R^1$, $R^2$, $R^3$, $R^4$, $R^5$, $R^6$, $R^7$, $R^8$, $R^9$ etc. Therefore, each 'R' group may be the same or different from each other R group. For the avoidance of doubt, the phrase "$R^1$ and $R^2$ are each independently selected from the group consisting of: H and a substituent" covers the following cases in which (1) $R^1$ is H and $R^2$ is a substituent, (2) $R^2$ is H and $R^1$ is a substituent, (3) $R^1$ is H and $R^2$ is H and (4) $R^1$ is a substituent and $R^2$ is a substituent. When $R^1$ is a substituent and $R^2$ is a substituent, $R^1$ and $R^2$ may be the same substituents or may be different substituents since they are each "independently selected" R groups. The same applies to other pairs of 'R' groups.

Throughout this specification, whenever a specific value is quoted for a temperature, pressure or time, the temperature, pressure or time quoted is approximate rather than the precise temperature, amount of pressure or amount of time. Nevertheless, the disclosure includes the precise value of any such variables which are approximately that value.

Throughout this specification, the term "substituent" means a non-hydrogen moiety, for example hydroxy, carboxy, carboxamido, imino, alkanoyl, cyano, cyanomethyl, nitro, amino, halogen (e.g. fluoro, chloro or bromo), $C_{1-6}$ haloalkyl (e.g. trifluoromethyl), $C_{1-6}$ alkoxy (e.g. methoxy, ethoxy or propoxy), $C_{1-6}$ haloalkoxy (e.g. trifluoromethoxy), hydrocarbyl or hydrocarbyloxy group. Suitably the non-hydrogen moiety does not detrimentally interfere with the curing process or with the stability of the composition. The just mentioned groups included in the definition of the term "substituent" may be each independently unsubstituted or substituted (wherever chemically possible) with from 1 to 5 substituents selected from the group consisting of: hydroxy, carboxy, carboxamido, imino, alkanoyl, cyano, cyanomethyl, nitro, amino, halogen (e.g. fluoro, chloro or bromo), $C_{1-6}$ alkyl (e.g. methyl, ethyl or propyl), $C_{1-6}$ haloalkyl (e.g. trifluoromethyl), $C_{1-6}$ alkoxy (e.g. methoxy, ethoxy or propoxy), $C_{1-6}$ haloalkoxy (e.g. trifluoromethoxy), $C_{3-6}$ cycloalkyl (e.g. cyclohexyl), aryl (e.g. phenyl), aryl-$C_{1-6}$ alkyl (e.g. benzyl) or $C_{1-6}$ alkyl aryl.

Hydrocarbyl and hydrocarbyloxy groups disclosed herein may have, for example, from 1 to 14, e.g. 1, 2, 3, 4, 5 or 6 carbon atoms.

Exemplary hydrocarbyl groups include those consisting of one or a combination of moieties selected from: alkyl, cycloalkyl, alkenyl, cycloalkenyl and aryl (e.g. phenyl), as is the case of phenylalkyl groups. For example, the term "hydrocarbyl" may be a non-hydrogen group selected from the group consisting of: alkyl (e.g. $C_{1-6}$ alkyl); alkenyl (e.g. $C_{2-6}$ alkenyl); aryl (e.g. phenyl); cycloalkyl (e.g. $C_{3-6}$ cycloalkyl); cycloalkenyl (e.g. $C_{4-6}$ cycloalkenyl); alkyl alkenyl (e.g. $C_{1-6}$ alkyl $C_{2-6}$ alkenyl), alkenyl alkyl (e.g. $C_{2-6}$ alkenyl $C_{1-6}$ alkyl), aryl alkyl (e.g. phenyl $C_{1-6}$ alkyl, for example benzyl); aryl alkyl (e.g. $C_{1-6}$ alkyl phenyl), alkyl cycloalkyl (e.g. $C_{1-6}$ alkyl $C_{4-6}$ cycloalkyl), cycloalkyl alkyl (e.g. $C_{3-6}$ cycloalkyl $C_{1-6}$ alkyl); cycloalkenyl alkyl (e.g. $C_{4-6}$ cycloalkenyl $C_{1-6}$ alkyl), and alkyl cycloalkyl (e.g. $C_{1-6}$ alkyl $C_{3-6}$ cycloalkyl). The above mentioned $C_{1-6}$ alkyl may be optionally interrupted by —O—, —S— or —NR—.

The term "package" includes a bottle for nail polish. The means for applying the nail coating composition to a nail may include a nail polish applicator. When the package is a bottle for nail polish and the means for applying the nail coating composition to a nail is a nail polish applicator, the nail polish applicator may extend from a removable cap of the bottle and be configured to enter the bottle when the cap is engaged with the bottle. The bottle may include a neck which is configured to engage the removable cap. The neck is typically a hollow cylinder or tube. The neck of the bottle and the removable cap may each be threaded such that the removable cap can be engaged and disengaged with the bottle by a twisting action. The nail polish applicator generally extends from an interior of the removable cap. In this configuration, the cap itself can be used as a handle which can be gripped when applying the nail polish to the nail. In an embodiment, the applicator includes a brush that the user dips into the nail polish to apply the same onto the user's nails. The brush typically includes a plurality of bristles extending axially or substantially axially from a shaft of the applicator and held onto the shaft of the applicator by a collar or adhesive. Suitable materials for the bristles of the brush include lacquered or unlacquered nylon. Alternatively, the applicator includes a dipstick which includes a sponge tip that the user may use to dip and apply the nail polish to the intended nail. The sponge tip may be wedge-shaped tip to allow more precision in application of the nail polish due to the relatively sharp edge of the wedge and thus provide finer lines than a brush. In any case, the applicator is typically configured so that the end of the applicator, i.e. the end of the applicator distal to the removable cap, is in contact with the interior surface of the base of the nail polish container. The volume of the nail polish bottle may be from about 1 ml to about 50 ml. In an embodiment, the nail polish bottle has a volume of about 3 ml, about 4 ml, about 7 ml, about 10 ml or about 15 ml.

1. Nail Composition:

In accordance with the present invention there is provided a nail coating composition comprising: a radiation curable component; and a thiol compound present in an amount of from about 5% to about 90% w/w of the nail coating composition.

The nail coating composition may include one or more additional components selected from photoinitiator(s), thickening agent(s), free-radical stabiliser(s), colorant(s), chelator(s) and adhesion promoter(s) amongst others. Further details of these components are given below.

In an embodiment, the viscosity of the nail composition is from about 500 to about 2000 cPs. Preferably, the viscosity of the nail composition is from about 750 to about 1500 cPs. Preferably, the viscosity of the nail composition is about 1000 cPs. All viscosity values herein refer to the viscosity measured at 25° C. The skilled person would be able to determine the necessary ratio of the components of the invention to achieve the desired viscosity. For example, adding a higher proportion of oligomer relative to monomer will increase the viscosity.

In an embodiment, the nail composition does not contain an aqueous phase.

1.1 Thiol Component:

The thiol component may include a mixture of more than one (e.g. two or three) different thiol compounds. The thiol component may consist of or consist essentially of a single thiol compound. Thus, when a particular thiol compound is recited below, the thiol component may include that thiol compound as the sole thiol compound or as one of a plurality of thiol compounds.

The term "thiol" includes compounds having from 1 to 10 —SH group(s). Each —SH group is bonded to a carbon atom. In other words, the thiol compounds have from 1 to 10-C—S—H moiety(ies). The thiol compound may be either simple or complex organic compounds having from 1 to 10 —SH group(s) at any position in the molecule. For example, the thiol compound may be either simple or complex organic compounds having from 1 to 10 —SH group(s) that are pendant or terminally positioned. It will be recalled that the term 1 to 10 means 1, 2, 3, 4, 5, 6, 7, 8, 9 or 10. Typically, the thiol compounds have at least two —C—S—H moieties, e.g. from 2 to 10 —C—S—H moieties, for example 2, 3, 4, 5, 6 or 7 —C—S—H moieties.

Generally, the carbon atom(s) to which the —SH group(s) is/are bonded form(s) part of an alkylenyl group, in particular a —$(CH_2)_n$— group, where the value of the integer n is not critical to the invention, but may be 1, 2, 3, 4, 5 or 6 for example.

The alkylenyl group of the thiol component may include one or more substituent group(s) as defined herein. Of course, the number of —SH group(s) present in the thiol compound is subject to the number of carbon atoms in the thiol compound (i.e. chemically impossible compounds are not included within the definition of thiol compounds).

In an embodiment, the thiol compound has a molecular weight of from about 100 to about 10,000 Da. In an embodiment, the thiol compound has a molecular weight of less than about 900 Da and preferably less than about 700 Da. For example, the thiol compound may have a molecular weight of about 200±50 Da, about 250±50 Da, about 300±50 Da, about 350±50 Da, about 400±50 Da, about 450±50 Da, about 500±50 Da, about 550±50 Da, about 600±50 Da, about 650±50 Da or about 700±50 Da.

In an embodiment, the thiol component is or comprises a polythiol compound having at least two thiol groups. In an embodiment, the thiol compound has from 2 to 10 —SH groups, i.e. 2, 3, 4, 5, 6, 7, 8, 9 or 10 such groups. In an embodiment, the thiol compound has from 2 to 5 —SH groups. In a preferred embodiment, the thiol compound has from 2 to 4 —SH groups. In further preferred embodiment, the thiol compound has 3 or 4 —SH groups.

In an embodiment, the thiol compound is present in the composition of the invention in an amount of no more than about 60% w/w; no more than about 50% w/w; no more than about 40% w/w; or no more than about 35% w/w. In an embodiment, the thiol compound is present in the composition of the invention in an amount of no more than about 30%; no more than about 25% w/w; no more than about 20% w/w. In an embodiment, the thiol compound is present in the composition of the invention in an amount of from about 5% to about 80% w/w; about 5% to about 70% w/w; about 5% to about 60% w/w; about 5% to about 50% w/w; about 5% to about 40% w/w; about 5% to about 30% w/w; about 5% to about 20% w/w; or about 5% to about 15% w/w. In an embodiment, the thiol compound is present in the composition of the invention in an amount of from about 10% to about 80% w/w; about 10% to about 70% w/w; about 10% to about 60% w/w; about 10% to about 50% w/w. The thiol compound may be present in an amount of from about 10% to about 30% w/w of the composition. In an embodiment, the thiol compound is present in the composition of the invention in an amount of from about 10% to about 15% w/w. In an embodiment, the thiol compound is present in the composition of the invention in an amount of from about 15% to about 20% w/w. In an embodiment, the thiol compound is present in the composition of the invention in an amount of from about 20% to about 25% w/w. In an embodiment, the thiol compound is present in the composition of the invention in an amount of from about 25% to about 30% w/w. For example, the thiol compound may be present in the composition of the invention in an amount of about 5%, about 6%, about 7%, about 8%, about 9%, about 10%, about 11%, about 12%, about 13%, about 14% or about 15% w/w or more.

By tetra or higher functional it is meant that the thiol has four or more —C—S—H moieties. By bis or tris functional it is meant that the thiol has two or three —C—S—H moieties.

In an embodiment, the thiol component consists of or consists essentially of a mixture of more than one (e.g. two or three) different thiol compounds. For example, the thiol component may include the following mixture of tri and tetra thiol components:

| % Tetra thiol | % Tri thiol |
| --- | --- |
| 10 | 0 |
| 8 | 3 |
| 6 | 6 |
| 4 | 8 |
| 2 | 11 |
| 0 | 15 |

In an embodiment, the thiol compound has a general structure:

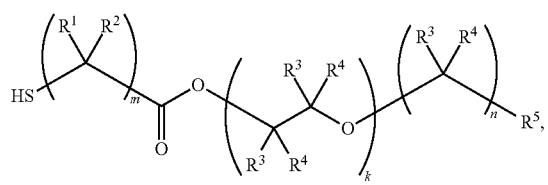

wherein
$R^1$, $R^2$, $R^3$, $R^4$ and $R^5$ are each independently selected from the group consisting of H and a substituent;
k is an integer of from 0 to 10, i.e. is 1, 2, 3, 4, 5, 6, 7, 8, 9 or 10; and
m and n are each independently an integer of from 1 to 10, i.e. are each independently 1, 2, 3, 4, 5, 6, 7, 8, 9 or 10.

In an embodiment, k is 0.

In an embodiment, m is an integer of from 1 to 5, preferably from 1 to 3, e.g. 1, 2 or 3.

In an embodiment, n is an integer of from 1 to 5, preferably from 1 to 3, e.g. 1, 2 or 3.

In an embodiment, $R^1$, $R^2$, $R^3$ and $R^4$ are each independently selected from the group consisting of: H, $C_{1-6}$ haloalkyl, $C_{1-6}$ alkoxy, $C_{1-6}$ haloalkoxy, hydrocarbyl and hydrocarbyloxy. In an embodiment, $R^1$, $R^2$, $R^3$ and $R^4$ are each independently selected from the group consisting of: H, $C_{1-6}$ alkyl, $C_{2-6}$ alkenyl, phenyl, $C_{3-6}$ cycloalkyl, $C_{4-6}$ cycloalkenyl, $C_{1-6}$ alkyl $C_{2-6}$ alkenyl, $C_{2-6}$ alkenyl $C_{1-6}$ alkyl, phenyl $C_{1-6}$ alkyl, $C_{1-6}$ alkyl phenyl, $C_{1-6}$ alkyl $C_{4-6}$ cycloalkyl, $C_{3-6}$ cycloalkyl $C_{1-6}$ alkyl, $C_{4-6}$ cycloalkenyl $C_{1-6}$ alkyl and $C_{1-6}$ alkyl $C_{3-6}$ cycloalkyl. In a preferred embodiment, $R^1$, $R^2$, $R^3$ and $R^4$ are each independently selected from the group consisting of: H and $C_{1-6}$ alkyl.

In an embodiment, $R^5$ is selected from the group consisting of: H and —$CR^{6a}R^{6b}R^{6c}$, wherein $R^{6a}$, $R^{6b}$ and $R^{6c}$ are each independently selected from the group consisting of: H, $C_{1-6}$ haloalkyl, $C_{1-6}$ alkoxy, $C_{1-6}$ haloalkoxy, hydrocarbyl, hydrocarbyloxy and

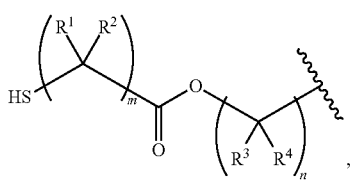

wherein $R^1$, $R^2$, $R^3$, $R^4$, m and n are as defined above.

In an embodiment, $R^5$ is $-CR^{6a}R^{6b}R^{6c}$, wherein $R^{6a}$, $R^{6b}$ and $R^{6c}$ are each independently selected from the group consisting of: H, $C_{1-6}$ alkyl and

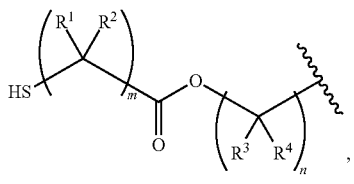

wherein $R^1$, $R^2$, $R^3$, $R^4$, m and n are as defined above.

In an embodiment, $R^{6a}$ is

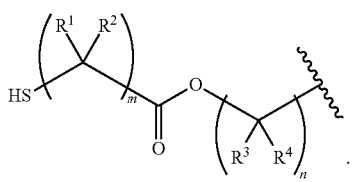

In an embodiment, the thiol compound has a general structure:

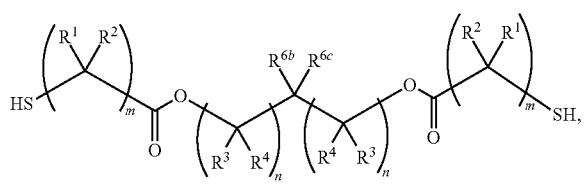

wherein $R^1$, $R^2$, $R^3$, $R^4$, $R^{6b}$, $R^{6c}$, m and n are as defined above.

In an embodiment, $R^{6b}$ is H.

In an embodiment, $R^{6b}$ is

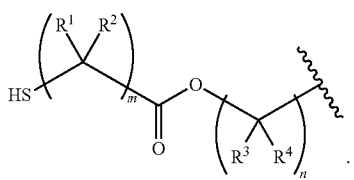

In an embodiment, $R^{6c}$ is H.

In an embodiment, $R^{6c}$ is

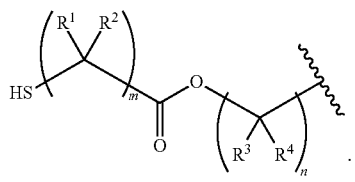

In an embodiment, $R^{6c}$ is $C_{1-6}$ alkyl, e.g. methyl, ethyl or propyl, preferably ethyl.

In an embodiment, $R^{6b}$ is H and $R^{6c}$ is H.

In an embodiment, $R^{6b}$ is

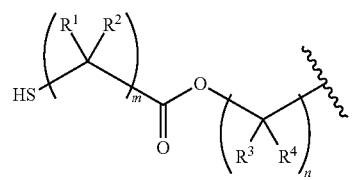

and $R^{6c}$ is $C_{1-6}$ alkyl, e.g. methyl, ethyl or propyl, preferably ethyl.

In an embodiment, $R^{6b}$ is

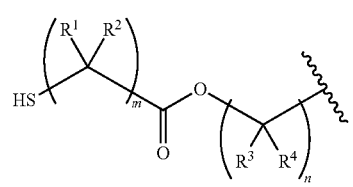

and $R^{6c}$ is

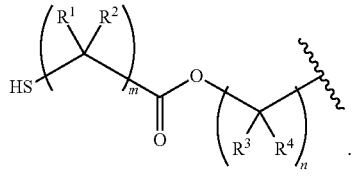

In an embodiment: k is 0; $R^5$ is $-CR^{6a}R^{6b}R^{6c}$; each of $R^{6a}$, $R^{6b}$ and $R^{6c}$ is

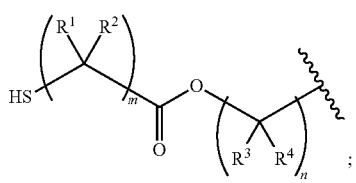

each $R^1$ is selected from the group consisting of: H and $C_{1-6}$ alkyl; each $R^2$ is H; each $R^3$ is H; each $R^4$ is H; each m is 2; and each n is 1.

In an embodiment: k is 0; $R^5$ is $-CR^{6a}R^{6b}R^{6c}$; each of $R^{6a}$ and $R^{6b}$ is

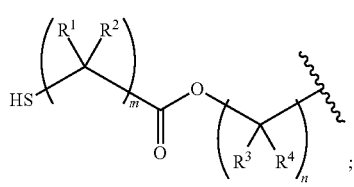

$R^{6c}$ is $C_{1-6}$ alkyl; each $R^1$ is selected from the group consisting of: H and $C_{1-6}$ alkyl; each $R^2$ is H; each $R^3$ is H; each $R^4$ is H; each m is 2; and each n is 1.

In an embodiment: $R^5$ is $-CR^{6a}R^{6b}R^{6c}$; each of $R^{6a}$, $R^{6b}$ and $R^{6c}$ is

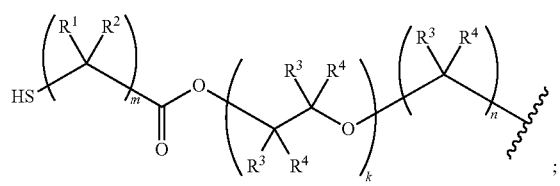

each $R^1$ is selected from the group consisting of: H and $C_{1-6}$ alkyl; each $R^2$ is H; each $R^3$ is H; each $R^4$ is H; each m is 2; and each n is 1.

In an embodiment: $R^5$ is $-CR^{6a}R^{6b}R^{6c}$; each of $R^{6a}$ and $R^{6b}$ is

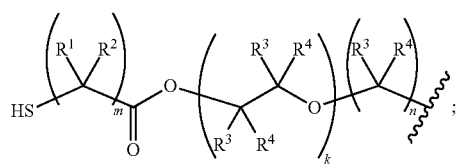

$R^{6c}$ is $C_{1-6}$ alkyl; each $R^1$ is selected from the group consisting of: H and $C_{1-6}$ alkyl; each $R^2$ is H; each $R^3$ is H; each $R^4$ is H; each m is 2; and each n is 1.

In an alternative embodiment, the thiol compound has a structure:

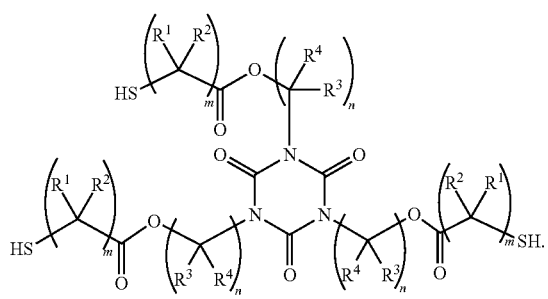

In an embodiment, the thiol compound is an ester of mercaptopropionic acid or mercaptobutyric acid.

In an embodiment, the thiol compound is pentaerythritol-4-mercaptopropionate or trimethylolpropane trimercaptopropionate.

In an embodiment, the thiol compound is:

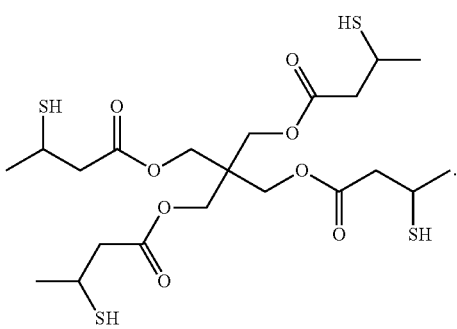 [SMILES: CC(S)CC(=O)OCC(COC(=O)CC(C)S)(COC(=O)CC(C)S)COC(=O)CC(C)S]

In an embodiment, the thiol compound is:

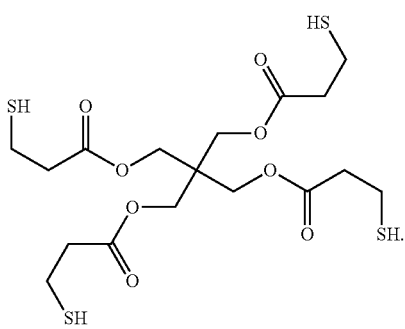 [SMILES: O=C(CCS)OCC(COC(=O)CCS)(COC(=O)CCS)COC(=O)CCS]

In an embodiment, the thiol compound is:

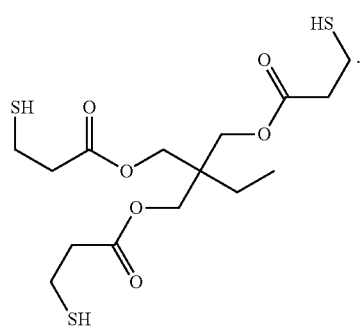 [SMILES: CCC(COC(=O)CCS)(COC(=O)CCS)COC(=O)CCS]

In an embodiment, the thiol compound is:

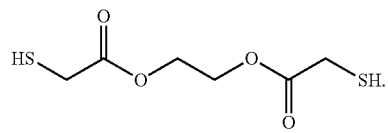 [SMILES: O=C(CS)OCCOC(=O)CS]

Without wishing to be bound by theory, it is thought that the thiol compound of the composition of the present invention reacts with the unsaturated bonds of the radiation curable component, see e.g. Kade et al, J. Polymer Science; Part A; Polymer Chemistry; Vol. 48; 743-750. Thus, it is thought that the following mechanism occurs:

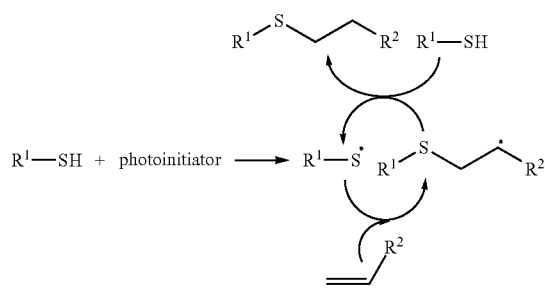

It is known that the above radical mechanism is insensitive to oxygen

Without wishing to be bound by theory, it is thought that the sulfur atoms of the thiol component interact with the sulfur atoms in the cysteine amino acid, which is found in the proteins of the nail itself. Thus, it is thought that a disulfide bond (—S—S—) might be formed between a cysteine sulfur atom and a sulfur atom of the thiol component. This would explain the improved adhesion of the nail composition of the present invention to the surface of the nail.

1.2 Radiation Curable Component:

The term "radiation curable component" includes compositions that are capable of curing under exposure to radiation. In an embodiment, the radiation curable components are UV radiation curable components. The general constituents and their proportions of a suitable composition will be known to a person skilled in the art. Curing includes the toughening or hardening of a material by cross-linking of polymer chains and, in the case of a radiation curable component, occurs as a result of the presence of chemical additives (such as photoinitiators) and exposure to radiation, e.g. UV radiation.

Suitable radiation curable components include a degree of unsaturation, e.g. at least one ethylenic bond. When the radiation curable component includes an ethylenic bond, it is this bond which is able to react (i.e. cross-link) with other materials in the composition, such as the thiol component. Examples of compounds having ethylenic unsaturation and being able to react with the thiol component include compounds having a vinyl ether, allyl ether, propenyl ether, allyl triazine, allyl ioscyanurate, alkene, acrylate, unsaturated ester, maleimide, methacrylate, acrylonitrile, styrene, diene or N-vinyl amide moiety, or a combination thereof. In this regard, the reaction between an ethylenic bond and the thiol component is described below. The reaction (i.e. cross-linking) between the different materials in the radiation curable composition results in curing of the composition.

Generally, a radiation curable composition will include an acrylate or methacrylate component. The term "acrylate" is used in the broad sense to include moieties having an alpha-beta unsaturated carboxyl group, i.e. moieties that contain a carbon-carbon double bond that is directly attached to a carbonyl carbon and should not necessarily be construed in the narrow sense as meaning $CH_2=CHCOO$—. The term "acrylate" thus discloses $CH_2=CHCOO$— as well as moieties having an alpha-beta unsaturated carboxyl group. The term "acrylate" includes methacrylate and both terms include reference to the acids as well as the esters. Each use of the term acrylate herein therefore include reference to alpha-beta unsaturated carboxylic acids and their esters, the compounds having the moiety $CH_2=CHCOO$— or $CH_2=C(CH_3)COO$—. In one implementation of the invention the acrylate is a methacrylate (i.e. $CH_2=C(CH_3)COO$—).

Typically, the acrylate, e.g. methacrylate component, is an acrylate-terminated oligomer, i.e. a short chain of monomers having an acrylate, e.g. methacrylate terminus. The skilled person is familiar with the term "oligomer" and will also readily be able to identify suitable acrylate-terminated oligomers. Further details of this component are given below.

The oligomer portion of the acrylate-terminated oligomer typically includes an epoxy or a urethane backbone, although other acrylate-terminated oligomers may also be used.

Additionally or alternatively, the radiation curable composition may include an allyl component. The term "allyl" is used in the broad sense to include moieties having an carbon-carbon double bond that is directly attached to an alkylene moiety and should not necessarily be construed in the narrow sense as meaning $CH_2=CHCH_2$—. The term "allyl" thus discloses $CH_2=CHCH_2$— even though it is not limited thereto.

Generally, a radiation curable composition will include acrylic acid ester monomers. The skilled person will also readily be able to identify suitable acrylic acid ester monomers. Further details of this component are given below.

Additionally or alternatively, a radiation curable composition may include an allyl terminated monomer component.

1.2.1 Acrylate-terminated Oligomer Component:

The term "acrylate-terminated oligomer component" includes an oligomer which terminates with an acrylate group at least one end. The oligomer component may include a mixture of more than one (e.g. two or three) different oligomers. The oligomer component may include a single oligomer. Thus, when a particular oligomer component is recited below, the oligomer component may include that oligomer component as the sole oligomer component or as one of a plurality of oligomer components. In other words, the term "acrylate-terminated oligomer component" includes an oligomer which has one or more pendent acrylate groups.

The term "acrylate" includes reference to moieties having an alpha-beta unsaturated carboxyl group, i.e. moieties that contain a vinyl group that is directly attached to a carbonyl carbon. The term "acrylate" thus includes moieties having the structure:

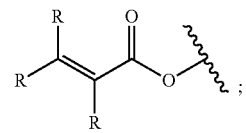

wherein the R groups in the above structure each independently represent H or a substituent. Optionally, the R groups each independently represent H or a $C_{1-10}$ alkyl group.

In an embodiment, the term "acrylate" refers to a moieties having an acrylate ($CH_2=CHCOO$—) or a methacrylate ($CH_2=CMeCOO$—) group.

In an embodiment, the acrylate moiety is a methacrylate moiety. This is beneficial since methacrylate ($CH_2=CMeCOO$—) is generally regarded as safer than ($CH_2=CHCOO$—).

The term "oligomer" includes compounds having a few monomer units, e.g. dimers, trimers and tetramers etc of monomers. An oligomer can, however, include more monomer units than this. For example, an oligomer may include from 5, 6, 7, 8, 9 or 10 monomer units or more, e.g. up to 100 monomer units. Oligomers can, however, include more than 100 monomer units. Thus, oligomers are manufactured from monomers that have been subjected to a finite degree of polymerization.

In an embodiment, the oligomer component has a molecular weight of from about 100 to about 20,000 Da. In an embodiment, the oligomer component has a molecular weight of from about 100 to about 5,000 Da. For example, the oligomer component may have a molecular weight of from about 100 to about 2,000 Da. The oligomer component may therefore have a molecular weight of about 500±100, about 600±100, about 700±100, about 800±100, about 900±100, about 1000±100, about 1100±100, about 1200±100, about 1300±100, about 1400±100 or about 1500±100 Da.

The oligomer component and its relative amount are selected such that the desired properties of the eventual nail composition (e.g. an end viscosity of 500 to 200 cPs) are achieved. Thus, to achieve the desired properties of the eventual nail composition, the oligomer component may include a relatively small amount (in quantity) of an oligomer having a high viscosity. In contrast, the oligomer component may include a relatively large amount (in quantity) of an oligomer having a low viscosity. The oligomer component may therefore include a small amount of a low viscosity component and a large amount of a high viscosity component or vice versa.

In an embodiment, the oligomer component has a viscosity, when measured at 25° C., of about 2000 to about 150000 cPs. In an embodiment, the oligomer component has a viscosity, when measured at 25° C., of about 3000 to about 10000 cPs. In an embodiment, the oligomer component has a viscosity, when measured at 25° C., of about 3500 to about 9000 cPs, e.g. about 4000±500, about 4500±500, about 5000±500, or about 5500±500. In an embodiment, the oligomer component has a viscosity, when measured at 25° C., of about 10000 to about 20000 cPs, e.g. 10000±1000, 11000±1000, 12000±1000, 13000±1000, 14000±1000, 15000±1000 or 16000±1000 cPs.

The oligomer component of the acrylate-terminated oligomer can include an oligomer selected from the group consisting of: epoxy oligomers, aliphatic and aromatic urethane oligomers, polyether and polyester oligomers and acrylic oligomers or a combination thereof.

In an embodiment, the acrylate-terminated oligomer component is present in the composition of the invention in an amount of from about 5% to about 80% w/w; 5% to about 70% w/w; about 5% to about 60% w/w; about 5% to about 50% w/w; about 5% to about 40% w/w; about 5% to about 30% w/w; or about 5% to about 20% w/w. In an embodiment, the acrylate-terminated oligomer component is present in the composition of the invention in an amount of from about 10% to about 60% w/w. In an embodiment, the acrylate-terminated oligomer component is present in the composition of the invention in an amount of from about 10% to about 20% w/w. In an embodiment, the acrylate-terminated oligomer component is present in the composition of the invention in an amount of from about 20% to about 30% w/w. In an embodiment, the acrylate-terminated oligomer component is present in the composition of the invention in an amount of from about 30% to about 40% w/w. In an embodiment, the acrylate-terminated oligomer component is present in the composition of the invention in an amount of from about 40% to about 50% w/w. In an embodiment, the acrylate-terminated oligomer component is present in the composition of the invention in an amount of from about 50% to about 60% w/w. For example, the acrylate-terminated oligomer component may be present in the composition of the invention in an amount of about 5%, about 6%, about 7%, about 8%, about 9%, about 10%, about 11%, about 12%, about 13%, about 14%, about 15%, about 16%, about 17%, about 18%, about 19% or about 20% w/w or more.

In an embodiment, the oligomer component is selected from the group consisting of: Genomer 4622® (an aromatic urethane acrylate oligomer), Polyester 03-849®, Genomer 4302® (an isocyanurate oligomer), Genomer 2253® (a modified epoxy acrylate oligomer), Genomer 4590/PP® (an aliphatic urethane acrylate oligomer), Genomer 2263® (an epoxy acrylate oligomer), Genomer 2259® (a modified epoxy acrylate oligomer), Genomer 3414® (a polyether acrylate oligomer), Genomer 2280® (a modified epoxy acrylate oligomer), Genomer 4312® (an aliphatic polyester urethane acrylate), Genomer 4316® (an aliphatic urethane acrylate oligomer), Genomer 4215® (an aliphatic urethane acrylate oligomer), UA00-0022® (an aliphatic urethane acrylate hydroxy functional oligomer), Genomer 2235® (an aliphatic epoxy acrylate oligomer) and Genomer 3611® (a polyester acrylate oligomer) and combinations thereof.

In an embodiment, the oligomer component is selected from the group consisting of: Genomer 3414® (a modified polyether acrylate oligomer), Genomer 03-956® (an aliphatic urethane dimethacrylate oligomer), Genomer 2280® (a modified bisphenol A epoxy diacrylate oligomer), Genomer 2281® (a modified bisphenol A epoxy diacrylate oligomer), Genomer 4425® (an aliphatic urethane acrylate in GPTA), Genomer 09-293® (an aliphatic urethane acrylate oligomer), Photomer 6210® (an aliphatic urethane oligomer), Ebecryl 3703® (an epoxy urethane acrylate oligomer) and Ebecryl 270® (an aliphatic urethane acrylate oligomer) and combinations thereof.

Each of the above oligomer components is commercially available. The Genomer® oligomers are available from Rahn®; the Photomer® oligomers are available from IGM Resins® and the Ebecryl® oligomers are available from Cytex®. Details of some of the properties of a number of these oligomers are provided in the "description" column in the examples below.

As mentioned above, the oligomer component may comprise more than one (e.g. two or three) oligomers. For example, the oligomer component may comprise a mixture of Genomer 03-956® and Photomer 6210®; Genomer 2280® and Genomer 03-956®; Genomer 03-956® and Genomer 09-293®; and Ebecryl 3703® and Genomer 03-956®.

This specification discloses nail compositions containing an oligomer component comprising or consisting of a liquid material which may undergo a cross-linking or polymerisation reaction to become a solid.

1.2.2 Allyl-terminated Oligomer Component:

The term "allyl-terminated oligomer component" includes an oligomer which terminates with term an allyl group at least one end. In other words, the term "allyl-terminated oligomer component" includes an oligomer which has one or more pendent allyl groups.

The oligomer component may include a mixture of more than one (e.g. two or three) different oligomers. The oligomer component may include a single oligomer. Thus, when a particular oligomer component is recited below, the oligomer component may include that oligomer component as the sole oligomer component or as one of a plurality of oligomer components.

The term "allyl" includes moieties having the structure:

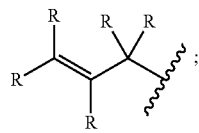

wherein the R groups in the above structure each independently represent H or a substituent. Optionally, the R groups each independently represent H or a $C_{1-10}$ alkyl group.

In an embodiment, the term "allyl" includes a moieties having a ($CH_2$=$CHCH_2$—) group.

In an embodiment, the allyl-terminated oligomer component is present in the composition of the invention in an amount of from about 5% to about 80% w/w; 5% to about 70% w/w; about 5% to about 60% w/w; about 5% to about 50% w/w; about 5% to about 40% w/w; about 5% to about 30% w/w; or about 5% to about 20% w/w. In an embodiment, the allyl-terminated oligomer component is present in the composition of the invention in an amount of from about 10% to about 60% w/w. In an embodiment, the allyl-terminated oligomer component is present in the composition of the invention in an amount of from about 10% to about 20% w/w. In an embodiment, the allyl-terminated oligomer component is present in the composition of the invention in an amount of from about 20% to about 30% w/w. In an embodiment, the allyl-terminated oligomer component is present in the composition of the invention in an amount of from about 30% to about 40% w/w. In an embodiment, the allyl-terminated oligomer component is present in the composition of the invention in an amount of from about 40% to about 50% w/w. In an embodiment, the allyl-terminated oligomer component is present in the composition of the invention in an amount of from about 50% to about 60% w/w. For example, the allyl-terminated oligomer component may be present in the composition of the invention in an amount of about 5%, about 6%, about 7%, about 8%, about 9%, about 10%, about 11%, about 12%, about 13%, about 14%, about 15%, about 16%, about 17%, about 18%, about 19% or about 20% w/w or more.

In an embodiment, the allyl-terminated component is an allyl ether or ester terminated component, i.e. a component terminated with $CH_2$=$CHCH_2$—O— or $CH_2$=$CHCH_2$—OC(=O)—. Examples of suitable allyl-terminated components include:

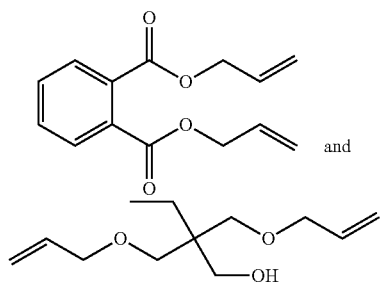

and

In an alternative embodiment, the allyl-terminated component comprises a reaction product of

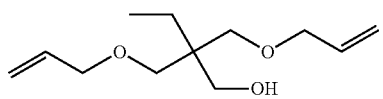

with toluene di-isocyanate, i.e.

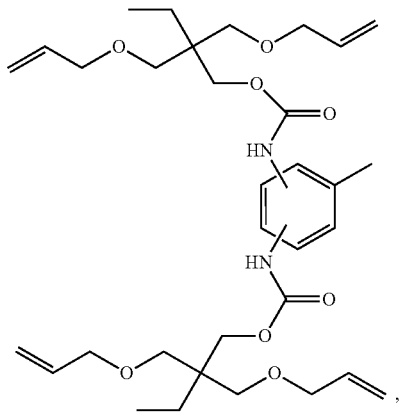

referred to hereinafter as "oligomer A".

1.2.3 Acrylic Acid Ester Monomer Component:

The term "acrylic acid ester monomer" includes compounds having an alpha-beta unsaturated carboxyl group, i.e. compounds that contain a vinyl group that is directly attached to a carbonyl carbon. The acrylic acid ester monomer component may include a mixture of more than one (e.g. two or three) different acrylic acid ester monomers. The acrylic acid ester monomer component may include a single acrylic acid ester monomer. Thus, when a particular acrylic acid ester monomer is recited below, the acrylic acid ester monomer component may include that monomer as the sole monomer or as one of a plurality of monomers. The term "acrylic acid ester monomer" thus includes compounds having the structure:

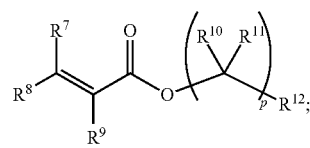

wherein $R^7$, $R^8$, $R^9$, $R^{10}$, $R^{11}$ and $R^{12}$ are each independently selected from the group consisting of: H and a substituent; and p is an integer of from 0 to 10. The term "acrylic acid ester monomer" thus also includes compounds having the structure:

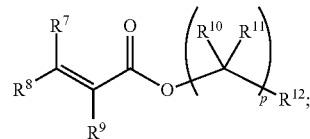

wherein $R^7$, $R^8$, $R^9$, $R^{10}$, $R^{11}$ and $R^{12}$ are each independently selected from the group consisting of: H and a substituent; and p is an integer of from 1 to 10.

In an embodiment, the acrylic acid ester monomer component has a molecular weight of from about 50, e.g. about 72 to about 1000 Da.

In an embodiment, the acrylic acid ester monomer includes from 1 to 10 alpha-beta unsaturated carboxyl group(s). The number of alpha-beta unsaturated carboxyl groups will affect the amount of cross-linking that occurs in the final composition when the composition is cured. The more alpha-beta unsaturated carboxyl groups the acrylic acid ester monomer has, the higher the degree of cross-linking. In an embodiment, the acrylic acid ester monomer includes 1, 2, 3, 4, 5 or 6 alpha-beta unsaturated carboxyl groups.

Without meaning to be bound by theory, it is though that the inclusion of acrylate monomers and resins modifies the cross linking and allows soak off of the cured nail polish to be achieved. This is desirable as the alternative to soaking off the nail polish is to remove it by abrasion and chipping, which can be detrimental to the nail itself.

In an embodiment, p is 0 and $R^{12}$ is H. In an embodiment, p is an integer of from 1 to 5, preferably from 1 to 4, e.g. 1, 2 or 3.

In an embodiment, $R^7$, $R^8$, $R^9$, $R^{10}$ and $R^{11}$ are each independently selected at each occurrence from the group consisting of: H, $C_{1-6}$ haloalkyl, $C_{1-6}$ alkoxy, $C_{1-6}$ haloalkoxy, hydrocarbyl and hydrocarbyloxy. In an embodiment, $R^7$, $R^8$, $R^9$, $R^{10}$ and $R^{11}$ are each independently selected at each occurrence from the group consisting of: H, $C_{1-6}$ alkyl, $C_{2-6}$ alkenyl, phenyl, $C_{3-6}$ cycloalkyl, $C_{4-6}$ cycloalkenyl, $C_{1-6}$ alkyl $C_{2-6}$ alkenyl, $C_{2-6}$ alkenyl $C_{1-6}$ alkyl, phenyl $C_{1-6}$ alkyl, $C_{1-6}$ alkyl phenyl, $C_{1-6}$ alkyl $C_{4-6}$ cycloalkyl, $C_{3-6}$ cycloalkyl $C_{1-6}$ alkyl, $C_{4-6}$ cycloalkenyl $C_{1-6}$ alkyl and $C_{1-6}$ alkyl $C_{3-6}$ cycloalkyl. In a preferred embodiment, $R^7$, $R^8$, $R^9$, $R^{10}$ and $R^{11}$ are each independently selected at each occurrence from the group consisting of: H and $C_{1-6}$ alkyl (e.g. methyl).

In an embodiment, $R^7$ and $R^8$ are each H.

In an embodiment, $R^9$ is selected from the group consisting of: H and $C_{1-6}$ alkyl (e.g. methyl).

In an embodiment, $R^{10}$ and $R^{11}$ are each independently selected at each occurrence from the group consisting of: H and $C_{1-6}$ alkyl (e.g. methyl).

In an embodiment, $R^{10}$ and $R^{11}$ are each H.

In an embodiment, $R^{10}$ and $R^{11}$ together with the atom to which they are bonded form a 3-6 membered cycloalkyl group. In an embodiment, $R^{10}$ and $R^{11}$ together with the atom to which they are bonded form a cyclopropyl, cyclobutyl, cyclopentyl or cyclohexyl group. In an embodiment, $R^{10}$ and $R^{11}$ together with the atom to which they are bonded form a bi- or tri-cyclic cycloalkyl group, e.g. an isobornyl group.

In an embodiment, $R^{12}$ is selected from the group consisting of: H, $-OR^{13}$ and $-CR^{12a}R^{12b}R^{12c}$; wherein $R^{12a}$, $R^{12b}$ and $R^{12c}$ are each independently selected from the group consisting of: H, $C_{1-6}$ haloalkyl, $C_{1-6}$ alkoxy, $C_{1-6}$ haloalkoxy, hydrocarbyl, hydrocarbyloxy and

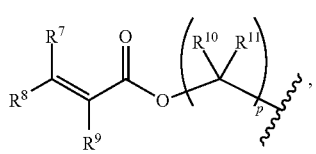

wherein $R^7$, $R^8$, $R^9$, $R^{10}$ and $R^{11}$ are each independently selected from the group consisting of: H and a substituent and each p is independently an integer of from 1 to 5; and $R^{13}$ is selected from the group consisting of: H and a substituent.

In an embodiment, $R^{12}$ is $-OH$.

In an embodiment, $R^{12}$ is $-OR^{13}$ and $R^{13}$ is a $C_{1-6}$ alkyl group.

In an embodiment, $R^{12}$ is H.

In an embodiment, $R^{12}$ is $-CR^{12a}R^{12b}R^{12c}$; wherein $R^{12a}$, $R^{12b}$ and $R^{12c}$ are each independently selected from the group consisting of: H, $C_{1-6}$ alkyl, and

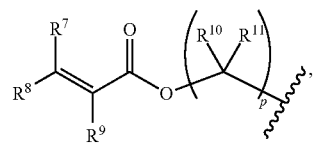

wherein each $R^7$, $R^8$, $R^9$, $R^{10}$ and $R^{11}$ is independently selected from the group consisting of: H and a substituent and each p is independently an integer of from 1 to 5.

In an embodiment: $R^{12}$ is $-CR^{12a}R^{12b}R^{12c}$; wherein $R^{12a}$, $R^{12b}$ and $R^{12c}$ are each independently

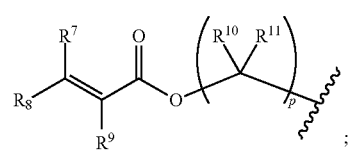

each $R^7$ is H; each $R^8$ is H; each $R^9$ is selected from the group consisting of: H and $C_{1-6}$ alkyl; each $R^{10}$ is H; each $R^{11}$ is H; and each p is 1.

In an embodiment: $R^{12}$ is $-CR^{12a}R^{12b}R^{12c}$; wherein $R^{12a}$ and $R^{12b}$ are each independently

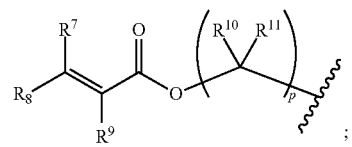

$R^{12c}$ is $C_{1-6}$ alkyl; each $R^7$ is H; each $R^8$ is H; each $R^9$ is selected from the group consisting of: H and $C_{1-6}$ alkyl; each $R^{10}$ is H; each $R^{11}$ is H; and each p is 1.

In an embodiment: $R^{12}$ is $-CR^{12a}R^{12b}R^{12c}$; wherein $R^{12a}$ and $R^{12b}$ are each independently

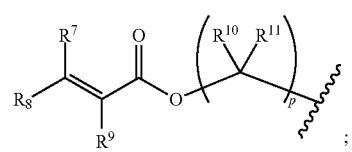

$R^{12c}$ is

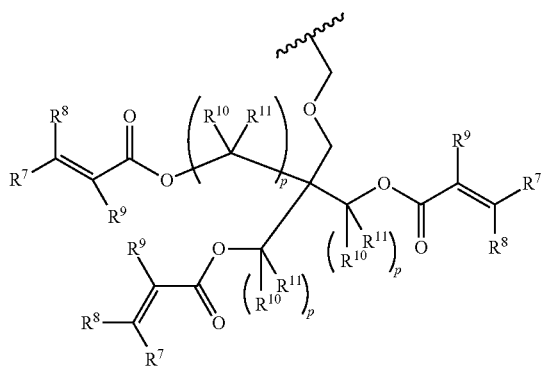

wherein each $R^7$, $R^8$, $R^9$, $R^{19}$ and $R^{11}$ is independently selected from the group consisting of: H and a substituent and each p is independently an integer of from 1 to 5.

In an embodiment, $R^{12c}$ is ethyl.

In an embodiment, $R^{12}$ is $-OR^{13}$.

In an embodiment, $R^{13}$ is:

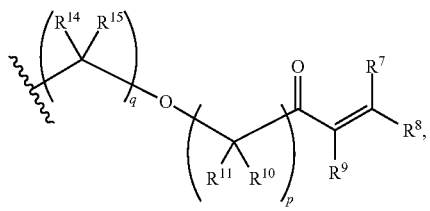

wherein $R^{14}$ and $R^{15}$ are each independently selected at each occurrence from the group consisting of: H and $C_{1-6}$ alkyl (e.g. methyl); q is an integer of from 1 to 5; and $R^7$, $R^8$, $R^9$, $R^{10}$, $R^{11}$ and p are as defined above.

In an embodiment, $R^{13}$ is:

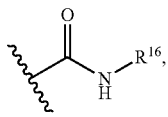

wherein $R^{16}$ is $C_{1-6}$ alkyl, e.g. methyl, ethyl, n-propyl, iso-propyl, n-butyl, sec-butyl or t-butyl.

In an embodiment, the acrylic acid monomer includes compounds having the structure:

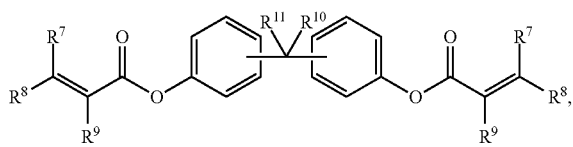

wherein $R^7$, $R^8$, $R^9$, $R^{19}$ and $R^{11}$ are each independently selected from the group consisting of: H and a substituent.

In an embodiment, the acrylic acid ester monomer component is a monofunctional monomer for example hydroxypropyl methacrylate.

In an embodiment, the acrylic acid ester monomer component is a difunctional monomer for example propoxylated neopentyl glycol diacrylate (Ebeccryl 145).

In an embodiment, the acrylic acid ester monomer component is a trifunctional monomer for example trimethylolpropane triacrylate.

In an embodiment, the acrylic acid ester monomer component is a tetrafunctional monomer for example dipentaerythritol tetraacrylate.

In an embodiment, the acrylic acid ester monomer component is butane-1,4-diol diacrylate.

In an embodiment, the acrylic acid ester monomer component is hexane-1,6-diol diacrylate.

In an embodiment, the acrylic acid ester monomer component is 2-hydroxyethyl 2-methylprop-2-enoate.

In an embodiment, the acrylic acid ester monomer component is isobornyl methacrylate.

In an embodiment, the acrylic acid ester monomer component is 2-((acryloyloxy)methyl)-2-ethylpropane-1,3-diyl diacrylate.

In an embodiment, the acrylic acid ester monomer component is 2-ethyl-2-((methacryloyloxy)methyl)propane-1,3-diyl bis(2-methylacrylate).

In an embodiment, the acrylic acid ester monomer component is 2-ethoxyethyl acrylate.

In an embodiment, the acrylic acid ester monomer component is bisphenol-A-dimethacrylate.

In an embodiment, the acrylic acid ester monomer component is ((2,2-dimethylpropane-1,3-diyl)bis(oxy))bis(propane-2,1-diyl)diacrylate.

In an embodiment, the acrylic acid ester monomer component is methacrylic acid.

In an embodiment, the acrylic acid ester monomer component is (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate).

In an embodiment, the acrylic acid ester monomer component is 2-[[(butylamino)carbonyl]oxy]ethyl acrylate.

In an embodiment, the acrylic acid ester monomer component is ethyl methacrylate.

In an embodiment, the acrylic acid ester monomer component is present in the composition of the invention in an amount of up to about 90% w/w e.g. from about 10% to about 90% w/w. The acrylic acid ester monomer component may be present in the composition in an amount of from about 10% to about 80% w/w; about 10% to about 70%; about 10% to about 60%; about 20% to about 70% w/w; about 20% to about 60% w/w; about 25% to about 55% w/w; about 25% to about 50% w/w; about 30% to about 45% w/w; or about 35% to about 45% w/w. In an embodiment, the acrylic acid ester monomer component is present in the composition of the invention in an amount of from about 10% to about 20%; about 20% to about 30%; about 30% to about 40%; about 40% to about 50%; or about 50% to about 60%. For example, the acrylic acid ester monomer component may be present in the composition of the invention in an amount of about 35%, about 36%, about 37%, about 38%, about 39%, about 40%, about 41%, about 42%, about 43%, about 44% or about 45% w/w or more.

1.2.4 Allyl Monomer Component:

The term "allyl monomer component" includes a compounds having an allyl group. In other words, the term "allyl monomer component" includes a compound which has one or more pendent allyl groups.

The allyl monomer component may include a mixture of more than one (e.g. two or three) different allyl monomers. The allyl monomer component may include a single allyl monomer. Thus, when a particular allyl monomer recited below, the allyl monomer component may include that monomer as the sole monomer or as one of a plurality of monomers.

The term "allyl monomer component" includes moieties having the structure:

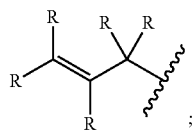

wherein the R groups in the above structure each independently represent H or a substituent. Optionally, the R groups each independently represent H or a $C_{1-10}$ alkyl group.

In an embodiment, the term "allyl monomer component" includes a moieties having a ($CH_2$=$CHCH_2$—) group.

In an embodiment, the allyl monomer component is present in the composition of the invention in an amount of from about 10% to about 80% w/w; about 10% to about 70%; about 10% to about 60%; about 10% to about 50% w/w; about 10% to about 40% w/w; about 10% to about 30% w/w; or about 10% to about 20% w/w. For example, the allyl monomer component may be present in the composition of the invention in an amount of about 10%, about 11%, about 12%, about 13%, about 14%, about 15%, about 16%, about 17%, about 18%, about 19% or about 20% w/w or more.

In an embodiment, the allyl monomer component is an allyl ether or ester monomer component, i.e. a component terminated with $CH_2$=$CHCH_2$—O— or $CH_2$=$CHCH_2$—OC(=O)—. Examples of suitable allyl monomer components include:

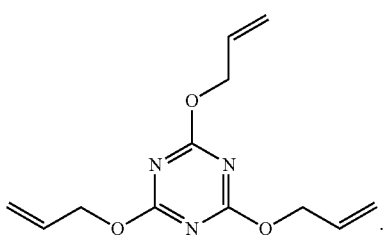 [SMILES: C=CCOc1nc(OCC=C)nc(OCC=C)n1]

1.3 Other Components:

As mentioned above, the nail coating composition may include one or more additional components selected from photoinitiators, thickening agents, free-radical stabilisers, colorants, chelators and adhesion promoters. Further details of these components are given below.

In an embodiment, the nail coating composition does not include a surfactant component. For example, in an embodiment, the nail coating composition does not include sorbitan sesquioleate, sorbitan dioleate, sorbitan trioleate, pentaerythritol dioleate or pentaerythritol trioleate.

1.3.1 Photoinitiator:

The term "photoinitiator" includes compounds that decompose free radicals when exposed to light. Therefore, photoinitiators form a free radical when exposed to light.

In an embodiment, the composition may include more than one photoinitiator (e.g. two, three or four photoinitiators). In an embodiment, the composition includes a single photoinitiator. Thus, when a particular photoinitiator is recited below, the nail composition may include that photoinitiator as the sole photoinitiator or as one of a plurality of photoinitiators.

Any photoinitiator compatible with the other components of the composition may be employed in the composition of the present invention. Suitable photoinitiators can be selected from either hydrogen abstracting or the free radical forming groups. Conveniently, the photoinitiators utilised in the present invention absorb light in the 200-450 nm region.

In an embodiment, the photoinitiator is a UVA activated photoinitiator. In an embodiment, the photoinitiator is a UVB activated photoinitiator. In an embodiment, the photoinitiator is a UVC activated photoinitiator. In an embodiment, the photoinitiator is a UVV activated photoinitiator. The skilled person is able to match the photoinitiator with the particular activation wavelength.

In an embodiment, the photoinitiator is selected from the group consisting of: Irgacure 369 (2-benzyl-2(dimethylamino)-1-[4-(4-morpholinyl)phenyl]-1-butanone), Genocure BDMM (2-benzyl-2 (dimethylamino)-1-[4-(4-morpholinyl)phenyl]-1-butanone), Irgacure 819 (phosphine oxide, phenyl bis(2,4,6-trimethyl benzoyl)), Lucirin BAPO (phenyl-bis-(2,4,6-trimethylbenzoyl)phosphine oxide, Genocure TPO (phosphine oxide, phenyl bis(2,4,6-trimethyl benzoyl)), Genocure LTM (a liquid photoinitiator blend), Lucirin TPO-L (ethyl-2,4,6-trimethylbenzoylphenylphosphinate), Genocure QC (D,L-camphorquinone), Genocure BDK (benzildmethylketal), Genocure PMP (2-methyl-1-(4-methylthiophenyl)-2-morpholinpropan-1-one), Genocure DMHA (dimethylhydroxyacetophenone), Genocure ITX (isopropylthioxanthone), Genocure EHA (2-ethylhexyl-4-dimethylamonobenzoate) and Genocure DETX (2,4-diethylthioxanthone).

In an embodiment, the photoinitiator is benzophenone.

In an embodiment, the photoinitiator is 2,2-dimethoxy-1,2 diphenylethan-1 one (known as Irgacure 651).

In an embodiment, the photoinitiator is 2,4,6 trimethylbenzoylphenyl-phosphineoxide (known as Genocure TPO).

In an embodiment, the photoinitiator is 1-hydroxycyclohexyl phenyl ketone (known as Irgracure 184) and also known as (1-hydroxycyclohexyl)(phenyl)methanone.

In an embodiment, the photoinitiator is oligo [2-hydroxy-2-methyl-1-(4-(1-methylvinyl)phenyl)]propanone (Ezacure One).

In an embodiment, the photoinitiator is bis(2,4,6-trimethylbenzoyl)-phenylphosphineoxide (Irgacure 819).

In an embodiment, the photoinitiator is methylbenzoylformate (Genocure MBF).

In an embodiment, the photoinitiator is present in the composition of the invention in an amount of from about 0.5% to about 20% w/w; about 0.5% to about 10% w/w; about 0.5% to about 5% w/w; or about 0.5% to about 3% w/w. In an embodiment, the photoinitiator is present in the composition of the invention in an amount of from about 4% to about 10% w/w; about 4% to about 9% w/w; about 4% to about 8% w/w; about 4% to about 7% w/w; about 4% to about 6% w/w; or about 4% to about 5% w/w. For example, the photoinitiator may be present in the composition of the invention in an amount of about 0.5%, about 0.75%, about 1.0%, about 1.25%, about 1.5%, about 1.75%, about 2.0%, about 2.25%, about 2.5%, about 2.75% or about 3.0% w/w.

1.3.2 Thickening Agents:

In an embodiment, the composition of the present invention further comprises a thickening agent. In an embodiment, the composition may include more than one thickening agent (e.g. two, three or four thickening agents). In an embodiment, the composition includes a single thickening agent. Thus, when a particular thickening agent is recited below, the nail composition may include that thickening agent as the sole thickening agent or as one of a plurality of thickening agents.

In an embodiment, the thickening agent is a fumed silica nanoparticle having a diameter of from about 5 nm to about 30 nm. The nanoparticles can be obtained from a company called Aerosil®. Examples of suitable nanoparticles includes: Aerosil R202® (14 nm), Aerosil R812® (7 nm), Aerosil 200® (12 nm) and Aerosil R 974® (12 nm).

In an embodiment, the thickening agent is a polymer of the acrylic acid ester monomer component.

In an embodiment, the thickening agent is Avalure 315®, which is described by the manufacturers, Lubrizol®, as an acrylic copolymer for cosmetics having a specific gravity of 1.1-1.2, a viscosity of 10-200 cPs (15% solids in $NH_4OH$ solution) and a particle size of 60-100 (% through 6 mesh) according to the data sheet dated March 2007.

In an embodiment the thickening agent is present in an amount of up to 10% w/w of the composition. It may be present in an amount of at least 1% w/w or the composition. In an embodiment the thickening agent is present in an amount of up to 7.5% w/w of the composition. For example, the thickening agent may be present in an amount of from about 3% to about 6% w/w of the composition. In an embodiment the polymers are present in an amount of up to 5% w/w of the composition. In an embodiment the polymers are present in an amount of up to 2.5% w/w of the composition.

The purpose of the polymer component is to adjust the viscosity of the eventual composition. Thus, the more polymer that is included in the composition, the more viscous the resulting mixture will be. The polymer can be used to substitute a portion of the oligomer portion. Thus, the composition may include no polymer, an amount of monomer and an amount of oligomer. If it is desired to reduce the amount of oligomer, then the amount of monomer can be increased and a polymer can be introduced in order to tune the viscosity of the resulting composition.

1.3.3 Free-radical Stabiliser:

In an embodiment, the composition of the present invention further comprises a free-radical stabiliser. The skilled person will be aware of suitable free-radical stabilisers that may be employed in the present invention. The free-radical stabiliser may be added to the composition in an amount of up to about 2% w/w of the composition. For example, the free-radical stabiliser may be added to the composition in an amount of about 0.5%, about 1.0%, about 1.5% or about 2.0% w/w of the composition.

In an embodiment, the composition may include more than one free-radical stabiliser (e.g. two, three or four free-radical stabilisers). In an embodiment, the composition includes a single free-radical stabiliser. Thus, when a particular free-radical stabiliser is recited below, the nail composition may include that free-radical stabiliser as the sole free-radical stabiliser or as one of a plurality of free-radical stabilisers.

In an embodiment, the free-radical stabiliser is selected from the group consisting of: hydroquinone, butyl hydroxytoluene, methylphenol, triphenylphosphite and Florstab UV-8®, which is described by the manufacturer, Kromachem®, as a blend of epoxy acrylate oligomer, polyester acrylate, plasticiser and stabiliser.

An amount of free-radical stabiliser may already be included in the raw materials of the present invention. When the raw materials of the present invention do not include a free-radical stabiliser, a free-radical stabiliser may be added to the composition.

1.3.4 Colorant:

In an embodiment, the composition of the present invention is a clear and colourless nail composition. This may be applied to a bare nail to make the nail attractive and shiny. Alternatively, in an embodiment, the composition of the present invention further comprises a mixture for example a dispersion of a colorant and an organic liquid. The term "organic liquid" may be used interchangeably with the term "carrier" or "solvent". In the latter embodiment, the nail composition is used to alter the colour and appearance of the nail.

Thus, in an embodiment, the composition of comprises a colorant and an organic liquid, and, taken together, the colorant and the organic liquid amount to up to about 10% w/w of the composition; up to about 7.5% w/w of the composition; up to about 5% w/w of the composition; or up to about 2.5% w/w of the composition.

In an embodiment, the colorant is present in an amount of from about 20% to about 80% of combined colorant and organic liquid.

In an embodiment, the colorant is a pigment. In an embodiment, the pigment is in particulate form.

In an embodiment, the composition may include more than one colorant or dispersion thereof (e.g. two, three or four colorants or dispersions thereof). In an embodiment, the composition includes a single colorant or dispersion thereof. Thus, when a particular colorant or dispersion thereof is recited below, the nail composition may include that colorant or dispersions thereof as the sole colorant or dispersion thereof or as one of a plurality of colorants or dispersions thereof.

In an embodiment, the pigment is selected from the group consisting of: Organic Red D&C Ca Lake CI Number 15850—5% (COD 8001), D&C Red 6 Ba Lake CI No 15850 (COD 8002); Black Iron Oxide CI No 77499 (COD 8004); FD&C Blue 1 Al Lake CI No 42090 (COD 8007); Titanium Dioxide CI No 77891-0.7% (COD 8008); FD&C Yellow 6 Al Lake CI No 15985 (COD 8010).

In an embodiment, the colorant is a photostable dye.

In an embodiment, the organic liquid is a volatile solvent, e.g. a polar organic ester or alcohol solvent such as, for example, butyl acetate, ethyl acetate and isopropanol. These particular organic liquids evaporate quickly and therefore allow the nail coating composition to dry quickly.

In an alternative embodiment, the organic liquid is not a volatile solvent. In an embodiment, the organic liquid is an oil. The benefit of using an oil is that the composition need not include volatile solvents which are generally regarded as not being environmentally friendly. When the organic liquid is an oil, it may also participate in the cross-linking reaction. This is because many oils include unsaturated bonds, e.g. carbon double bonds. In an embodiment, therefore, the oil comprises or is an ethylenically unsaturated oil. The oil may be or comprise a fish or vegetable oil. The oil may therefore comprise a mixture of fatty acid glycerides, e.g. a mixture comprising at least one ethylenically unsaturated fatty acid compound. As described above, the thiol compound of the composition is able to react with unsaturated bonds. Thus, not wishing to be bound by theory, it is thought that the oil, when unsaturated, is covalently incorporated into the final cross-linked structure.

In an embodiment, the oil is selected from the group consisting of: castor oil, dehydrated castor oil, cotton seed oil, fish oil, linseed oil, menhaden oil, oiticaca oil, palm kernel oil, perilla oil, safflower oil, sardine oil, soybean oil and tung oil.

1.3.5 Chelator:

In an embodiment, the composition further comprises up to 2% w/w of a chelator. In an embodiment, the composition comprises up to 1% w/w of a chelator. In an embodiment, the composition comprises up to 0.1% w/w of a chelator. In an embodiment, the composition comprises up from about 0.01 to about 0.1% w/w of a chelator. A chelator is particularly important when the composition comprises particular colorants or pigments. For example, many pigments include a relatively high metal content. Certain metals, e.g. Cu and Fe, are known to trigger free-radical polymerisation. Thus, the presence of a chelating compound can 'trap' the metal ions and prevent any undesired free-radical polymerisation that may otherwise have been caused by the presence of the metal in the pigment or colorant.

In an embodiment, the composition may include more than one chelator (e.g. two, three or four chelators). In an embodiment, the composition includes a single chelator. Thus, when a particular chelator is recited below, the nail composition may include that chelator as the sole chelator or as one of a plurality of chelators.

In an embodiment, the chelator is ethylene diamine tetraacetic acid (EDTA). In an embodiment, the chelator is EDTA in the form of the sodium salt.

In an embodiment, the chelator is 1-Hydroxy Ethylidene-1,1-Diphosphonic Acid (HEDP).

1.3.6 Adhesion Promoter:

In an embodiment, the composition further comprises an adhesion promoter. The adhesion promoter may be in an amount of up to about 10% w/w of the composition. For example, the composition may further comprise up to about 9%, up to about 8%, up to about 7%, up to about 6%, up to about 5%, up to about 4%, up to about 3% or up to about 2% w/w of an adhesion promoter. The adhesion promoter may be in an amount of at least about 0.5% w/w e.g. at least 1% w/w as in the case of from about 1% to about 8% w/w.

In an embodiment, the composition further comprises more than one (e.g. a mixture of two, three or four) adhesion promoters. In an embodiment, the composition includes a single adhesion promoter. Thus, when a particular adhesion promoter is recited below, the nail composition may include that adhesion promoter as the sole adhesion promoter or as one of a plurality of adhesion promoters.

In an embodiment, the adhesion promoter is Gamma-Glycidoxylpropyltrimethoxysilane (Silquest A-187).

In an embodiment, the adhesion promoter is 1,2,4,5-benzenetetracarboxylicacid,1,4-bis[2-[(2-methyl-1-oxo-2-propen-1-yl)oxy]-1-[[(2-methyl-1-oxo-2-propen-1-yl)oxy]methyl]ethyl]ester which is known in the art as pyromellitic glycerol dimethacrylate.

In an embodiment, the adhesion promoter is acrylic acid.

In an embodiment, the adhesion promoter is methacrylic acid.

In an embodiment, the adhesion promoter is 2-(methacryloyloxy)ethyl acetoacetate.

In an embodiment, the additional adhesion promoter is mono-2-(methacryloyloxy)ethyl succinate.

Methods of Applying the Nail Composition to the Nail:

The invention provides a method of applying a composition of the disclosure to a nail comprising contacting the nail with the composition. In this method, therefore, the composition is applied directly to the nail and not through a so-called "prebond" or "tie" layer. However, there is contemplated an alternative method in which a pre-bond or tie layer is used.

The nail composition of the present invention can be applied to the nail by any conventional apparatus, such as by dipping a nail polish brush into the composition and painting it onto the nail. It is an optional feature of the methods of the invention that only a single coating of the composition is applied.

Once the nail composition has been applied to the nail, the nail is then exposed to radiation. In an embodiment, the nail is exposed to radiation for a period of time of up to about 5 minutes, optionally up to about 4 minutes, for example up to about 3 minutes and for example up to about 2 minutes, e.g. less than one minute.

Accordingly, once the nail composition has been applied to the nail, the nail may then be exposed to radiation for a period of time of from about 30 seconds to about 5 minutes, optionally from about 1 minute to about 5 minutes, optionally from about 1 minute to about 4 minutes, for example about 1 minute to about 3 minutes and for example from about 1 minute to about 2 minutes. In an embodiment, the nail may then be exposed to radiation for a period of time of up to about one minute.

In an embodiment, the radiation comprises or is sunlight. In an alternative embodiment, the radiation comprises or is UV radiation from an electrical radiation source. A commercially available UV radiation source or lamp will be suitable for the methods of the present invention. In an embodiment, the radiation is emitted from an LED array.

In an embodiment, the radiation to which the nail composition is exposed has a wavelength of from about 200 nm to about 760 nm. In an embodiment, the radiation to which the nail composition is exposed has a wavelength of from about 200 nm to about 450 nm. In an embodiment, the radiation to which the nail composition is exposed has a wavelength of from about 310 nm to about 425 nm, e.g. about 315 to about 380 nm. In an embodiment, the radiation to which the nail composition is exposed has a wavelength of from about 400 nm to about 450 nm.

The intensity of the radiation is normally measured at a particular wavelength. For example, the conventional wavelength at which the intensity of light is measured is 365 nm. In an embodiment, the intensity of the radiation to which the nail composition is exposed has an intensity of from about 0.5 to about 2 mW/cm$^2$ at about 365 nm. This intensity range is generally regarded in the art as being "low intensity". In an embodiment, the intensity is from about 0.7 to about 1.2 mW/cm$^2$ at 365 nm. For example the intensity is may be about 0.9 mW/cm$^2$ at 365 nm or 1.5 mW/cm$^2$ at 365 nm.

In an embodiment, the intensity of the radiation is measured across all wavelengths. In an embodiment, the intensity of radiation is from about 0.1 mW/cm$^2$ to about 100 mW/cm$^2$. For example, a device such as a UV Power Puck can be used. This kind of device is an electro-optic radiometer that measures and displays the total UV energy and UV intensity. The UV Power Puck measures four different ranges of ultraviolet wavelengths at the same time (i.e. UVA (320-390 nm), UVB (280-320 nm), UVC (250-260 nm) and UVV (395-445 nm). In an embodiment, the total intensity of the radiation is from about 5 to about 50 mW/cm$^2$.

Typically, once the nail coating composition of the invention has been exposed to UV radiation and has cured, it is not necessary to carry out a further step of wiping uncured nail composition from the outer surface of the coated nail. Generally, the outer surface is substantially tack-free after curing with UV radiation. This is a benefit of the coating compositions of the invention over the prior art compositions.

When it is desired to remove the cured nail composition, the cured nail varnish composition may conveniently be removed by using a conventional nail polish remover (e.g. acetone). The nail polish remover and the cured nail varnish composition are suitably maintained in contact for about 1 minute to about 10 minutes. It is thought that contacting the cured composition with the nail polish remover breaks down the cross-linked network. After the cured nail composition has been contacted with the conventional nail polish remover, the cured nail composition can be wipe off the nail in the same manner that a conventional solvent-based (i.e. non-UV curable composition) can be removed from a nail. It is not necessary to use abrasion to remove the cured nail composition of the present invention as is necessary with other conventional UV curable nail polish compositions.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

The following examples provide various formulations falling within the scope of the present invention. The resulting formulations have a viscosity in the desired range of 500-2000 cPs, are cured after only 2 minutes exposure to UV light, have the desired property of being smooth, dry and well adhered to the nail, soak off very easily when it is desired to remove the nail composition and have good stability.

Each of the formulations was tested to determine whether the nail composition has the required properties of good adhesion, good stability and good durability. All of the following formulations were found to have these properties.

Additionally, when the coated nails were soaked in acetone, the nail polish was easily removed without requiring abrasion.

Adhesion

The uncured coating is applied to a glass slide in a thin layer and cured for 2 minutes under a standard 36W UV lamp. The adhesion of the cured coating is then tested using a method described by Schlossman et al, J. Soc. Cosmet. Chem. 32, 43-52 (January/February 1981) called the "cellophane adhesion test".

In the tape adhesion test, the coating is deeply scribed with a razor blade in the shape of a Greek letter lambda and a hash sign. This cut is made 1 inch (about 2.5 cm) high and ½ inch (about 1.25 cm) wide at the base. A piece of ordinary ¾ inch (about 1.9 cm) cellophane is laid over its entire surface with a hard rubber eraser. A tab large enough to be grasped firmly with the fingers is left well above the figure. The tape is then removed by pulling rapidly and evenly toward the bottom of the test panel.

The squares of coating that are removed are counted and an estimate of the amount of coating removed is given. All of the formulations have a percentage of coating removed of less than 10%.

In contrast, a conventional solvent based nail polish was tested using the same procedure. The uncured coating is applied to a glass slide in a thin layer and left to dry for 24 hours at room temperature. This period of time is much longer than conventional nail polish would be left to dry when applying it to a nail. The adhesion of the cured coating is then tested using the "cellophane adhesion test" as described above. The conventional solvent based nail polishes have a percentage coating removed of between 30 and 100% depending on the brand tested. Thus, the nail polishes of the present invention have much better adhesive properties than conventional nail polishes.

Stability

After testing the adhesion of the formulations (above) the stability of the formulations is then tested. This is done to mimic the shelf life of the formulation in the bottle.

The coating is placed in a nail polish bottle with brush and put into ovens at two different temperatures. The uncured product has to remain mobile and usable for >5 days at 55° C. and >6 hours at 82° C.

If the formulation passes both of these tests then the shelf life in the bottle will be at least one year. A shelf life of this length means that the formulation is commercially viable.

Durability on the Nail

Finally, two coats of nail polish are applied to a number of test subjects nails. The first coat is fully cured for two minutes before a second coat is applied which is also cured for two minutes. We then wait for feedback from the test subjects as to the number of days the coating lasted before chipping or delamination appeared.

This test is very useful as it demonstrates the effects of real-life activities on the durability of the nail composition. Each of the below formulations lasted for a minimum time before chipping of at least 5 days. This length of time is considered in the industry to be a good performance from a quality nail polish. A conventional nail polish will typically last for one or two days before chipping.

Example 1

| Ingredients | Description | Amount |
|---|---|---|
| Genomer 2280 - Rahn | Modified bisphenol A epoxy diacrylate For radically curable inks, coatings and adhesives Data Sheet dated 29 Aug. 2006 version 1.002/HS Functionality: 2; Colour index: ≤6 Gardner Viscosity: 5000 cPs/25 C.; Density: 1.20 | 43.3 |
| Butane-1,4-diol diacrylate | | 12.0 |
| 2-ethyl-2-((methacryloyloxy)methyl)propane-1,3-diyl bis(2-methylacrylate) | | 18.1 |
| Pentaerythritol tetrakis (3-mercaptopropionate) | | 12.0 |
| EDTA (Na Salt) | | 0.1 |
| Triphenyl-phosphite (TPhPh) | | 0.4 |
| (1-hydroxycyclohexyl)(phenyl)methanone (Irgacure 184) | | 6.0 |
| 2,2 Dimethoxy 1,2 diphenylethan-1-one (Irgacure 651) | | 1.2 |
| Organic Red D&C Ca Lake CI Number 15850 - 5% (COD 8001) | | 6.0 |
| Inorganic White Titanium Dioxide CI 77891 - 0.7% (COD 8008) | | 0.8 |
| | | 100 |

Example 2

| Ingredient | Description | Amount |
|---|---|---|
| Genomer 2280 - Rahn | Modified bisphenol A epoxy diacrylate For radically curable inks, coatings and adhesives Data Sheet dated 29 Aug. 2006 version 1.002/HS Functionality: 2; Colour index: ≤6 Gardner Viscosity: 5000 cPs/25 C.; Density: 1.20 | 24.9 |
| Genomer 03-956 - Rahn | Aliphatic urethane Dimethacrylate Monomer free for radically curable inks, coatings and adhesives. Data Sheet dated 7 May 2009, version 1.001/RW Colour Index: ≥3 Gardener; Viscosity: 8700 cPs/25° C.; Tg: 43° C.; Density: 1.11; Functionality: 2 | 14.9 |
| Butane-1,4-diol diacrylate | | 9.0 |
| 2-ethyl-2-((methacryloyloxy)methyl)propane-1,3-diyl bis(2-methylacrylate) | | 16.9 |
| Acrylic Acid | | 2.0 |
| Pentaerythritol tetrakis (3-mercaptopropionate) | | 19.9 |
| Tetrasodium EDTA | | 0.05 |
| Triphenyl-phosphite | | 0.3 |
| Capstone FS-3100 | Partially fluorinated alcohol substituted glycol | 0.2 |
| (1-hydroxycyclohexyl)(phenyl)methanone (Irgacure 184) | | 5.0 |
| 2,2 Dimethoxy 1,2 diphenylethan-1-one (Irgacure 651) | | 1.0 |
| Bis(2,4,6-trimethylbenzoyl)-phenylphosphineoxide (Irgacure 819) | | 0.5 |
| Organic Red D&C Ca Lake CI Number 15850 - 5% (COD 8001) | | 4.8 |
| Inorganic White Titanium Dioxide CI 77891 - 0.7% (COD 8008) | | 0.7 |
| | | 100.0 |

Example 3

| Ingredient | Description | Amount |
|---|---|---|
| Ebecryl 270 - Cytec | Aliphatic Urethane Acrylate Radcure Technical Publication Pub No 210115E version C Viscosity: 135000 cPs/25 C. Density: 1.1 Functionality: 2 Mwt: 1500 | 27.3 |
| Butane-1,4-diol diacrylate | | 13.7 |
| Bisphenol-A-Dimethacyrlate | | 13.7 |
| Nitro cellulose | | 2.2 |
| Acrylic Acid | | 2.7 |
| 2-ethyl-2-((methacryloyloxy)methyl)propane-1,3-diyl bis(2-methylacrylate) | | 15.5 |//
| Pentaerythritol tetrakis (3-mercaptopropionate) | | 10.9 |
| Tetrasodium EDTA | | 0.03 |
| (1-hydroxycyclohexyl)(phenyl)methanone (Irgacure 184) | | 5.5 |
| Benzophenone | | 2.7 |
| Bis(2,4,6-trimethylbenzoyl)-phenylphosphineoxide (Irgacure 819) | | 0.5 |
| Organic Red D&C Ca Lake CI Number 15850 - 5% (COD 8001) | | 4.8 |
| Inorganic White Titanium Dioxide CI 77891 - 0.7% (COD 8008) | | 0.7 |
| | | 100.0 |

Example 4

| Ingredient | Description | Amount |
|---|---|---|
| Genomer 09-293 - Rahn | Aliphatic urethane acrylate Monomer free for radically curable inks, coatings and adhesives. Data Sheet dates 7 May 2009, version: 1.001/RW Functionality: 2 Colour Index: ≤3 Gardner Viscosity: 16000 cPs/25 C.; Density: 1.14 | 12.4 |
| Propoxylated (2) neopentyl glycol diacrylate (((2,2-dimethylpropane-1,3-diyl)bis(oxy))bis(propane-2,1-diyl) diacrylate) | | 10.5 |
| Pentaerythritol tetrakis (3-mercaptobutylate) | | 59.0 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.9 |
| Tetrasodium EDTA | | 0.03 |
| Capstone FS-3100 | Partially fluorinated alcohol substituted glycol | 0.3 |
| Gamma-Glycidoxylpropyltrimethoxysilane (Silquest A-187) | | 0.5 |
| Pyromellitic Dianhydride | CAS # 146166-65-6 | 3.3 |
| Glycerol Dimethacrylate | | |
| Florstab UV 8 (Kromachem) | A blend of epoxy acrylate oligomer, polyester acrylate, plasticiser and inhibitor | 0.8 |
| Methylbenzoylformate (Genocure MBF) | | 3.8 |
| 2,2 Dimethoxy 1,2 diphenylethan-1-one (Irgacure 651) | | 1.0 |
| Phenyl bis(2,4,6-trimethylbenzoyl)-phosphine oxide (Irgacure 819) | | 0.5 |
| Organic Red D&C Ca Lake CI Number 15850 - 5% (COD 8001) | | 4.5 |
| Inorganic White Titanium Dioxide CI 77891 - 0.7% (COD 8008) | | 0.6 |
| | | 100.0 |

Example 5

| Ingredient | Description | Amount |
|---|---|---|
| Genomer 03-956 - Rahn | Aliphatic urethane Dimethacrylate Monomer free for radically curable inks, coatings and adhesives. Data Sheet dated 7 May 2009, version 1.001/RW Colour Index: ≥3 Gardener Viscosity: 8700 cPs/25° C. Tg: 43° C.; Density: 1.11; Functionality: 2 | 59.8 |
| Propoxylated (2) neopentyl glycol diacrylate-(((2,2-dimethylpropane-1,3-diyl)bis(oxy))bis(propane-2,1-diyl) diacrylate) | | 4.6 |
| 2-((acryloyloxy)methyl)-2-ethylpropane-1,3-diyl diacrylate | | 4.6 |
| Pentaerythritol tetrakis (3-mercaptopropionate) | | 13.8 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.8 |
| Tetrasodium EDTA | | 0.03 |
| Capstone FS-3100 | Partially fluorinated alcohol substituted glycol | 0.3 |
| Gamma-Glycidoxylpropyltrimethoxysilane (Silquest A-187) | | 0.4 |
| Pyromellitic Dianhydride Glycerol Dimethacrylate | CAS # 146166-65-6 | 3.2 |
| Florstab UV 8 (Kromachem) | A blend of epoxy acrylate oligomer, polyester acrylate, plasticiser and inhibitor | 0.8 |
| Methylbenzoylformate (Genocure MBF) | | 3.7 |
| 2,2 Dimethoxy 1,2 diphenylethan-1-one (Irgracure 651) | | 0.9 |
| Phenyl bis(2,4,6-trimethylbenzoyl)-phosphine oxide (Irgacure 819) | | 0.4 |
| Organic Red D&C Ca Lake CI Number 15850 - 5% (COD 8001) | | 4.2 |
| Inorganic White Titanium Dioxide CI 77891 - 0.7% (COD 8008) | | 0.6 |
| | | 100.0 |

Example 6

| Ingredient | Description | Amount |
|---|---|---|
| Genomer 09-293 - Rahn | Aliphatic urethane acrylate Monomer free for radically curable inks, coatings and adhesives. Data Sheet dates 7 May 2009, version: 1.001/RW Functionality: 2 Colour Index: ≤3 Gardner; Viscosity: 16000 cPs/25 C. Density: 1.14 | 13.8 |
| Propoxylated (2) neopentyl glycol diacrylate (((2,2-dimethylpropane-1,3-diyl)bis(oxy))bis(propane-2,1-diyl) diacrylate) | | 55.2 |
| Pentaerythritol tetrakis (3-mercaptopropionate) | | 12.0 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 4.6 |

-continued

| Ingredient | Description | Amount |
|---|---|---|
| Tetrasodium EDTA | | 0.03 |
| Capstone FS-3100 | Partially fluorinated alcohol substituted glycol | 0.3 |
| Gamma-Glycidoxylpropyltrimethoxysilane (Silquest A-187) | | 0.4 |
| Pyromellitic Dianhydride Glycerol Dimethacrylate | CAS # 146166-65-6 | 3.2 |
| Florstab UV 8 (Kromachem) | A blend of epoxy acrylate oligomer, polyester acrylate, plasticiser and inhibitor | 0.8 |
| Methylbenzoylformate (Genocure MBF) | | 3.7 |
| 2,2 Dimethoxy 1,2 diphenylethan-1-one (Irgracure 651) | | 0.9 |
| Phenyl bis(2,4,6-trimethylbenzoyl)-phosphine oxide (Irgacure 819) | | 0.4 |
| Organic Red D&C Ca Lake CI Number 15850 - 5% (COD 8001) | | 4.2 |
| Inorganic White Titanium Dioxide CI 77891 - 0.7% (COD 8008) | | 0.6 |
| | | 100.0 |

Example 7

| Ingredient | Description | Amount |
|---|---|---|
| Genomer 03-956 - Rahn | Aliphatic urethane Dimethacrylate; Monomer free for radically curable inks, coatings and adhesives.; Data Sheet dated 7 May 2009, version 1.001/RW; Colour Index: ≥3 Gardener; Viscosity: 8700 cPs/25° C.; Tg: 43° C.; Density: 1.11; Functionality: 2 | 8.7 |
| Avalure 315 - Lubrizol | Acrylic copolymer for cosmetics.; Data Sheet dated March 2007; Specific Gravity: 1.1-1.2; Viscosity: 10-200 cPs (15% solids in NH4OH solution); Particle size: 60-100 (% thru 6 mesh) | 4.6 |
| Genomer 09-293 - Rahn | Aliphatic urethane acrylate; Monomer free for radically curable inks, coatings and adhesives.; Data Sheet dates 7 May 2009, version: 1.001/RW; Functionality: 2; Colour Index: ≤3 Gardner; Viscosity: 16000 cPs/ 25 C.; Density: 1.14 | 15.5 |
| 2-Hydroxyethyl 2-methylprop-2-enoate | | 6.2 |
| Isobornyl Methacrylate | | 4.6 |
| Propoxylated (2) neopentyl glycol diacrylate (((2,2-dimethylpropane-1,3-diyl)bis(oxy))bis(propane-2,1-diyl) diacrylate) | | 12.2 |
| 2-ethyl-2-((methacryloyloxy)methyl)propane-1,3-diyl bis(2-methylacrylate) | | 12.7 |
| Methacrylic acid | | 1.7 |
| Trimethylolpropane tris(3-mercaptopropionate) | 2-ethyl-2-(((3-mercaptopropanoyl)oxy)methyl)propane-1,3-diyl bis(3-mercaptopropanoate)/CAS 33007-83-9 | 16.4 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.4 |
| Tetrasodium EDTA | | 0.02 |
| Capstone FS-3100 | Partially fluorinated alcohol substituted glycol | 0.3 |
| Gamma-Glycidoxylpropyltrimethoxysilane (Silquest A-187) | | 0.5 |
| Pyromellitic glycerol dimethacrylate | CAS # 146166-65-6 | 3.4 |
| Methylbenzoylformate (Genocure MBF) | | 3.9 |

-continued

| Ingredient | Description | Amount |
|---|---|---|
| 2,2 Dimethoxy 1,2 diphenylethan-1-one (Irgracure 651) | | 1.0 |
| Flurostab UV-8 (Kromachem) | A blend of epoxy acrylate oligomer, polyester acrylate, plasticiser and inhibitor | 0.8 |
| Phenyl bis(2,4,6-trimethylbenzoyl)-phosphine oxide. (Irgacure 819) | | 0.5 |
| Organic Red D&C Ca Lake CI Number 15850 - 5% (COD 8001) | | 4.1 |
| Inorganic White Titanium Dioxide CI 77891 - 0.7% (COD 8008) | | 0.6 |
| | | 100.0 |

Example 8

| Ingredient | Description | Amount |
|---|---|---|
| Ebecryl 270 - Cytec | Aliphatic Urethane Acrylate Radcure Technical Publication Pub No 210115E version C Viscosity: 135000 cPs/25 C. Density: 1.1 Functionality: 2 Mwt: 1500 | 39.0 |
| Propoxylated (2) neopentyl glycol diacrylate (((2,2-dimethylpropane-1,3-diyl)bis(oxy))bis(propane-2,1-diyl) diacrylate) | | 13.0 |
| 2-ethyl-2-((methacryloyloxy)methyl)propane-1,3-diyl bis(2-methylacrylate) | | 19.5 |

-continued

| Ingredient | Description | Amount |
|---|---|---|
| Pentaerythritol tetra (3-mercaptopropionate) | | 13.0 |
| Tetrasodium EDTA | | 0.10 |
| Triphenyl-phosphite | | 0.4 |
| (1-hydroxycyclohexyl)(phenyl)methanone (Irgacure 184) | | 6.5 |
| 2,2 Dimethoxy 1,2 diphenylethan-1-one (Irgracure 651) | | 1.3 |
| Phenyl bis(2,4,6-trimethylbenzoyl)-phosphine oxide (Irgacure 819) | | 0.7 |
| Organic Red D&C Ca Lake CI Number 15850 - 5% (COD 8001) | | 5.6 |
| Inorganic White Titanium Dioxide CI 77891 - 0.7% (COD 8008) | | 0.9 |
| | | 100.0 |

Example 9

| Ingredient | Description | Amount |
|---|---|---|
| Genomer 03-956 - Rahn | Aliphatic urethane Dimethacrylate; Monomer free for radically curable inks, coatings and adhesives.; Data Sheet dated 7 May 2009, version 1.001/RW; Colour Index: ≥3 Gardener; Viscosity: 8700 cPs/25° C.; Tg: 43° C.; Density: 1.11; Functionality: 2 | 8.7 |
| Avalure 315 - Lubrizol | Acrylic copolymer for cosmetics.; Data Sheet dated March 2007; Specific Gravity: 1.1-1.2; Viscosity: 10-200 cPs (15% solids in NH4OH solution); Particle size: 60-100 (% thru 6 mesh) | 4.6 |
| Genomer 09-293 - Rahn | Aliphatic urethane acrylate; Monomer free for radically curable inks, coatings and adhesives.; Data Sheet dates 7 May 2009, version: 1.001/RW; Functionality: 2; Colour Index: ≤3 Gardner; Viscosity: 16000 cPs/25 C.; Density: 1.14 | 15.5 |
| 2-Hydroxyethyl 2-methylprop-2-enoate | | 6.2 |
| Isobornyl Methacrylate | | 4.6 |
| Propoxylated (2) neopentyl glycol diacrylate (((2,2-dimethylpropane-1,3-diyl)bis(oxy))bis(propane-2,1-diyl) diacrylate) | | 12.2 |
| 2-ethyl-2-((methacryloyloxy)methyl)propane-1,3-diyl bis(2-methylacrylate) | | 12.7 |
| Methacrylic acid | | 1.7 |
| Ethylene glycol bisthioglycolate | CAS 123-81-9 | 16.4 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.4 |
| Tetrasodium EDTA | | 0.02 |

| Ingredient | Description | Amount |
|---|---|---|
| Capstone FS-3100 | Partially fluorinated alcohol substituted glycol | 0.3 |
| Gamma-Glycidoxylpropyltrimethoxysilane (Silquest A-187) | | 0.5 |
| Pyromellitic glycerol dimethacrylate | CAS # 146166-65-6 | 3.4 |
| Methylbenzoylformate (Genocure MBF) | | 3.9 |
| 2,2 Dimethoxy 1,2 diphenylethan-1-one (Irgracure 651) | | 1 |
| Flurostab UV-8 (Kromachem) | A blend of epoxy acrylate oligomer, polyester acrylate, plasticiser and inhibitor | 0.8 |
| Phenyl bis(2,4,6-trimethylbenzoyl)-phosphine oxide (Irgacure 819) | | 0.5 |
| Organic Red D&C Ca Lake CI Number 15850 - 5% (COD 8001) | | 4.1 |
| Inorganic White Titanium Dioxide CI 77891 - 0.7% (COD 8008) | | 0.6 |
| | | 100 |

Example 10

| Ingredient | Description | Amount |
|---|---|---|
| Genomer 03-956 - Rahn | Aliphatic urethane Dimethacrylate; Monomer free for radically curable inks, coatings and adhesives.; Data Sheet dated 7 May 2009, version 1.001/RW Colour Index: ≥3 Gardener; Viscosity: 8700 cPs/25° C.; Tg: 43° C.; Density: 1.11; Functionality: 2 | 9.0 |
| Avalure 315 - Lubrizol | Acrylic copolymer for cosmetics.; Data Sheet dated March 2007; Specific Gravity: 1.1-1.2; Viscosity: 10-200 cPs (15% solids in NH4OH solution); Particle size: 60-100 (% thru 6 mesh) | 5.4 |
| Genomer 09-293 - Rahn | Aliphatic urethane acrylate; Monomer free for radically curable inks, coatings and adhesives.; Data Sheet dates 7 May 2009, version: 1.001/RW; Functionality: 2; Colour Index: ≤3 Gardner; Viscosity: 16000 cPs/25 C.; Density: 1.14 | 18.1 |
| 2-Hydroxyethyl 2-methylprop-2-enoate | | 7.2 |
| Isobornyl Methacrylate | | 5.4 |
| Propoxylated (2) neopentyl glycol diacrylate (((2,2-dimethylpropane-1,3-diyl)bis(oxy))bis(propane-2,1-diyl) diacrylate) | | 9.9 |
| 2-ethyl-2-((methacryloyloxy)methyl)propane-1,3-diyl bis(2-methylacrylate) | | 13.6 |
| Methacrylic acid | | 1.8 |
| Pentaerythritol tetrakis (3-mercaptopropionate) | | 17.2 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.7 |
| Tetrasodium EDTA | | 0.03 |
| Capstone FS-3100 | Partially fluorinated alcohol substituted glycol | 0.3 |
| Gamma-Glycidoxylpropyltrimethoxysilane (Silquest A-187) | | 0.5 |
| Pyromellitic glycerol dimethacrylate (PMGDM) | 1,2,4,5-Benzenetetracarboxylicacid,1,4-bis[2-[(2-methyl-1-oxo-2-propen-1-yl)oxy]-1-[[(2-methyl-1-oxo-2-propen-1-yl)oxy]methyl]ethyl]ester | 3.6 |
| Methylbenzoylformate (Genocure MBF) | | 3.6 |
| 2,2 Dimethoxy 1,2 diphenylethan-1-one (Irgracure 651) | | 0.9 |
| Flurostab UV-8 (Kromachem) | A blend of epoxy acrylate oligomer, polyester acrylate, plasticiser and inhibitor | 0.8 |
| | | 100.0 |

Example 11

| Ingredient | Description | Amount |
| --- | --- | --- |
| Genomer 03-956 - Rahn | Aliphatic urethane Dimethacrylate; Monomer free for radically curable inks, coatings and adhesives.; Data Sheet dated 7 May 2009, version 1.001/RW; Colour Index: ≥3 Gardener; Viscosity: 8700 cPs/25° C.; Tg: 43° C.; Density: 1.11; Functionality: 2 | 8.6 |
| Avalure 315 - Lubrizol | Acrylic copolymer for cosmetics.; Data Sheet dated March 2007; Specific Gravity: 1.1-1.2; Viscosity: 10-200 cPs (15% solids in NH4OH solution); Particle size: 60-100 (% thru 6 mesh) | 5.1 |
| Genomer 09-293 - Rahn | Aliphatic urethane acrylate; Monomer free for radically curable inks, coatings and adhesives.; Data Sheet dates 7 May 2009, version: 1.001/RW; Functionality: 2; Colour Index: ≤3 Gardner; Viscosity: 16000 cPs/ 25 C.; Density: 1.14 | 17.1 |
| 2-Hydroxyethyl 2-methylprop-2-enoate | | 6.6 |
| Isobornyl Methacrylate | | 5.1 |
| Propoxylated (2) neopentyl glycol diacrylate (((2,2-dimethylpropane-1,3-diyl)bis(oxy))bis(propane-2,1-diyl) diacrylate) | | 9.5 |
| 2-ethyl-2-((methacryloyloxy)methyl)propane-1,3-diyl bis(2-methylacrylate) | | 12.9 |
| Methacrylic acid | | 1.7 |
| Pentaerythritol tetrakis (3-mercaptopropionate) | | 16.3 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.6 |
| Tetrasodium EDTA | | 0.03 |
| Capstone FS-3100 | Partially fluorinated alcohol substituted glycol | 0.3 |
| Gamma-Glycidoxylpropyltrimethoxysilane (Silquest A-187) | | 0.4 |
| Pyromellitic glycerol dimethacrylate | 1,2,4,5-Benzenetetracarboxylicacid,1,4-bis[2-[(2-methyl-1-oxo-2-propen-1-yl)oxy]-1-[[(2-methyl-1-oxo-2-propen-1-yl)oxy]methyl]ethyl]ester | 3.4 |
| Methylbenzoylformate (Genocure MBF) | | 3.4 |
| 2,2 Dimethoxy 1,2 diphenylethan-1-one (Irgracure 651) | | 0.9 |
| Flurostab UV-8 (Kromachem) | A blend of epoxy acrylate oligomer, polyester acrylate, plasticiser and inhibitor | 0.7 |
| Bis(2,4,6-trimethylbenzoyl)-phenylphosphineoxide (Irgacure 819) | | 0.5 |
| Organic Red D&C Ca Lake CI Number 15850 - 5% (COD 8001) | | 4.3 |
| Inorganic White Titanium Dioxide CI 77891 - 0.7% (COD 8008) | | 0.6 |
| | | 100.0 |

Example 12

| Ingredient | Description | Amount |
|---|---|---|
| Oligomer A | (structure shown) | 43 |
| Pentaerythritol tetrakis (3-mercaptobutylate) | | 50 |
| Silane 1-110 | | 0.5 |
| Methylbenzoylformate (Genocure MBF) | | 4.0 |
| 2,2 Dimethoxy 1,2 diphenylethan-1-one (Irgacure 651) | | 1.0 |
| Tetrasodium EDTA | | 1.0 |
| Tri Phenyl Phosphite | | 0.5 |
| | | 100 |

Example 13

| Ingredients | Description | Amount |
|---|---|---|
| Ebecryl 270 - Cytec | Aliphatic Urethane AcrylateRadcure Technical Publication Pub No 210115E version C Viscosity: 135000 cPs/ 25 C. Density: 1.1 Functionality: 2 Mwt: 1500 | 38.9 |
| Propoxylated (2) neopentyl glycol diacrylate (((2,2-dimethylpropane-1,3-diyl)bis(oxy))bis(propane-2,1-diyl) diacrylate) | | 13.0 |
| 2-ethyl-2-((methacryloyloxy)methyl)propane-1,3-diyl bis(2-methylacrylate) | | 19.5 |
| Pentaerythritol tetrakis (3-mercaptopropionate) | | 13.0 |
| EDTA (Na Salt) | | 0.1 |
| Triphenyl-phosphite (TPhPh) | | 0.4 |
| (1-hydroxycyclohexyl)(phenyl)methanone (Irgacure 184) | | 6.5 |
| 2,2 Dimethoxy 1,2 diphenylethan-1-one (Irgracure 651) | | 1.3 |
| Organic Red D&C Ca Lake CI Number 15850 - 5% (COD 8001) | | 6.5 |
| Inorganic White Titanium Dioxide CI 77891 - 0.7% (COD 8008) | | 0.9 |
| | | 100 |

Example 14

| Ingredient | Description | |
|---|---|---|
| Genomer 2281 - Rahn | Modified bisphenol A epoxy diacrylate For radically curable inks, coatings and adhesives Data Sheet dated 29 Aug. 2006 version 1.002/HS Functionality: 2 Colour index: ≤6 Gardner Viscosity: 5000 cPs/25 C. Density: 1.20 | 39.8 |
| Genomer 03-956 - Rahn | Aliphatic urethane Dimethacrylate Monomer free for radically curable inks, coatings and adhesives. Data Sheet dated 7 May 2009, version 1.001/RW Colour Index: ≥3 Gardener Viscosity: 8700 cPs/25° C. Tg: 43° C. | 4.9 |

-continued

| Ingredient | Description | |
|---|---|---|
| | Density: 1.11 | |
| | Functionality: 2 | |
| 1,6-hexane diol diacrylate | | 11.7 |
| 2-ethyl-2-((methacryloyloxy)methyl)propane-1,3-diyl bis(2-methylacrylate) | | 13.7 |
| Methacrylic Acid | | 0.5 |
| Pentaerythritol tetrakis (3-mercaptopropionate) | | 16.6 |
| Tetrasodium EDTA | | 0.05 |
| Capstone FS-3100 | Partially fluorinated alcohol substituted glycol | 0.3 |
| Gamma-Glycidoxylpropyltrimethoxysilane (Silquest A-187) | | 0.5 |
| Florstab UV-8 (Kromachem) | A blend of epoxy acrylate oligomer, polyester acrylate, plasticiser and inhibitor | 0.8 |
| Methylbenzoylformate (Genocure MBF) | | 3.9 |
| Phenyl bis(2,4,6-trimethylbenzoyl)-phosphine oxide (Irgacure 819) | | 2.0 |
| Organic Red D&C Ca Lake CI Number 15850 - 5% (COD 8001) | | 4.8 |
| Inorganic White Titanium Dioxide CI 77891 - 0.7% (COD 8008) | | 0.7 |
| | | 100.0 |

Comparative Example 15

| Ingredient | Description | Amount |
|---|---|---|
| Genomer 03-956 - Rahn | Aliphatic urethane Dimethacrylate; Monomer free for radically curable inks, coatings and adhesives.; Data Sheet dated 7 May 2009, version 1.001/RW; Colour Index: ≥3 Gardener; Viscosity: 8700 cPs/25° C.; Tg: 43° C.; Density: 1.11; Functionality: 2 | 10.2 |
| Avalure 315 - Lubrizol | Acrylic copolymer for cosmetics.; Data Sheet dated March 2007; Specific Gravity: 1.1-1.2; Viscosity: 10-200 cPs (15% solids in NH4OH solution); Particle size: 60-100 (% thru 6 mesh) | 4.6 |
| Genomer 09-293 - Rahn | Aliphatic urethane acrylate; Monomer free for radically curable inks, coatings and adhesives.; Data Sheet dates 7 May 2009, version: 1.001/RW; Functionality: 2; Colour Index: ≤3 Gardner; Viscosity: 16000 cPs/25 C.; Density: 1.14 | 15.5 |
| 2-Hydroxyethyl 2-methylprop-2-enoate | | 6.2 |
| Isobornyl Methacrylate | | 8.5 |
| Propoxylated (2) neopentyl glycol diacrylate (((2,2-dimethylpropane-1,3-diyl)bis(oxy))bis(propane-2,1-diyl) diacrylate) | | 12.2 |
| 2-ethyl-2-((methacryloyloxy)methyl)propane-1,3-diyl bis(2-methylacrylate) | | 12.7 |
| Methacrylic acid | | 1.7 |
| Trimethylolpropane tris(3-mercaptopropionate) | 2-ethyl-2-(((3-mercaptopropanoyl)oxy)methyl)propane-1,3-diyl bis(3-mercaptopropanoate)/CAS 33007-83-9 | 11.0 |
| Dipentaerythritol Hexaacrylate | (2-[[3-[(1-oxoallyl)oxy]-2,2-bis[[(1-oxoallyl)oxy]methyl]propoxy]methyl]-2-[[(1-oxoallyl)oxy]methyl]-1,3-propanediyl diacrylate) | 2.4 |
| Tetrasodium EDTA | | 0.02 |
| Capstone FS-3100 | Partially fluorinated alcohol substituted glycol | 0.3 |
| Gamma-Glycidoxylpropyltrimethoxysilane (Silquest A-187) | | 0.5 |
| Pyromellitic glycerol dimethacrylate | CAS # 146166-65-6 | 3.4 |
| Methylbenzoylformate (Genocure MBF) | | 3.9 |

-continued

| Ingredient | Description | Amount |
|---|---|---|
| 2,2 Dimethoxy 1,2 diphenylethan-1-one (Irgracure 651) | | 1.0 |
| Flurostab UV-8 (Kromachem) | A blend of epoxy acrylate oligomer, polyester acrylate, plasticiser and inhibitor | 0.8 |
| Phenyl bis(2,4,6-trimethylbenzoyl)-phosphine oxide. (Irgacure 819) | | 0.5 |
| Organic Red D&C Ca Lake CI Number 15850 - 5% (COD 8001) | | 4.1 |
| Inorganic White Titanium Dioxide CI 77891 - 0.7% (COD 8008) | | 0.6 |
| | | 100.0 |

The composition of this example is the same as the composition of example 7, except that the composition of example 7 has a trifunctional thiol level of 16.4% whereas the composition of this example has a reduced level of trifunctional thiol (11.0%). The level of Genomer 03-956 and isobornyl methacrylate were increased by 1.5 and 3.9% respectively to retain the same formulation weight. Whereas the composition of example 7 demonstrates the desired dry to touch properties, the composition of this example is slightly tacky after curing (which is not desirable).

The invention claimed is:

1. A package comprising:
   (i) a nail coating composition comprising:
      a radiation curable component comprising:
         an acrylate-terminated oligomer in combination with at least one acrylate monomer; or
         an allyl-terminated oligomer in combination with at least one acrylate monomer and at least one acrylate-terminated oligomer; or
         an allyl-terminated oligomer in combination with at least one acrylate monomer;
         wherein the acrylate-terminated oligomer and/or the allyl-terminated oligomer is present in an amount of from about 5% to about 80% w/w of the composition;
         wherein the acrylate monomer is present in an amount of from about 10% to about 40% w/w of the composition; and
      a thiol component comprising a compound containing two or more SH groups, wherein: (i) when the thiol component is a bis functional thiol it is present in an amount of from 15% to about 90% w/w of the nail coating composition; (ii) when the thiol component is a tris functional thiol it is present in an amount of from 15% to about 90% w/w of the nail coating composition; and (iii) when the thiol component is a tetra or higher functional component it is present in an amount of from 5% to about 90% w/w of the nail coating composition; and
   (ii) a means for applying the nail coating composition to a nail.

2. The package of claim 1, wherein the composition is curable by subjecting it to 200 nm to 450 nm wavelength radiation.

3. The package of claim 1, wherein when the thiol component is a tetra or higher functional component it is present in an amount of from 10% to about 90% w/w of the nail coating composition.

4. The package of claim 1, wherein the thiol component has a general structure

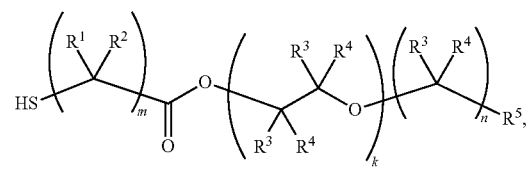

wherein $R^1$, $R^2$, $R^3$ and $R^4$ are each independently selected from the group consisting of H and a substituent;

$R^5$ is $—CR^{6a}R^{6b}R^{6c}$, wherein $R^{6a}$ is

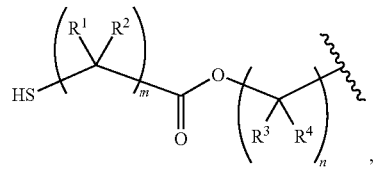

$R^{6b}$ and $R^{6c}$ are each independently selected from the group consisting of: H, $C_{1-6}$ alkyl and

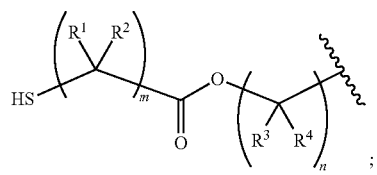

k is an integer of from 0 to 10; and m and n are each independently an integer of from 1 to 10.

5. The package of claim 4, wherein k is 0.

6. The package of claim 4, wherein m is an integer of from 1 to 3.

7. The package of claim 4, wherein n is an integer of from 1 to 3.

8. The package of claim 4, wherein $R^1$, $R^2$, $R^3$ and $R^4$ are each independently selected from the group consisting of: H and $C_{1-6}$ alkyl.

9. The package of claim 4, wherein $R^{6b}$ is H.

10. The package of claim 4, wherein $R^{6b}$ is

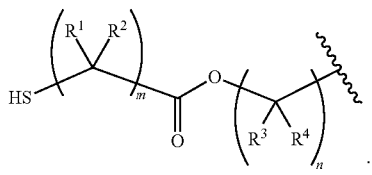

11. The package of claim 4, wherein $R^{6c}$ is H.

12. The package of claim 4, wherein $R^{6c}$ is

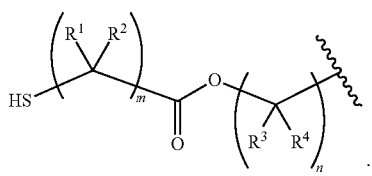

13. The package of claim 4, wherein $R^{6c}$ is $C_{1-6}$ alkyl.

14. The package of claim 1, wherein the thiol component comprises a compound which is selected from the group consisting of:

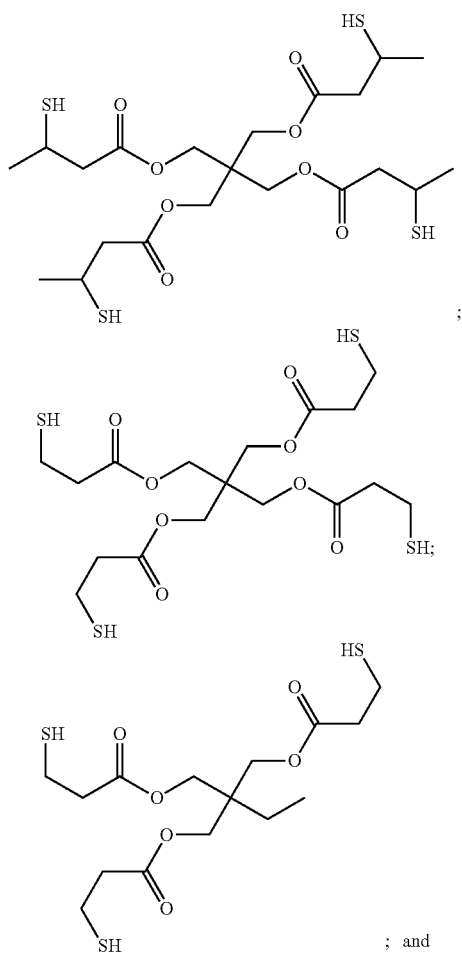

; and

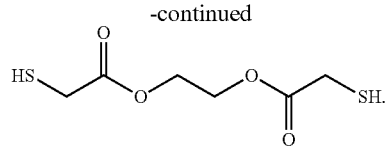

15. The package of claim 1, wherein the acrylate-terminated oligomer is an oligomer terminating with a $CH_2$=CHCOO— or $CH_2$=C(CH_3)COO— group.

16. The package of claim 1, wherein the acrylate-terminated oligomer and/or the allyl-terminated oligomer is present in an amount of from about 5% to about 70% w/w of the composition.

17. The package of claim 1, wherein the acrylate-terminated oligomer and/or the allyl-terminated oligomer includes an epoxy backbone.

18. The package of claim 1, wherein the acrylate-terminated oligomer and/or the allyl-terminated oligomer includes a urethane backbone.

19. The package of claim 1, wherein the acrylate-terminated oligomer and/or the allyl-terminated oligomer has a viscosity, when measured at 25° C., of about 2000 to about 150000 cPs.

20. The package of claim 1, wherein the acrylate monomer is present in an amount of from about 10% to about 30% w/w of the composition.

21. The package of claim 1, wherein the radiation curable component comprises a photoinitiator.

22. The package of claim 21, wherein the photoinitiator is present in an amount of from about 0.1% to about 20% w/w of the composition.

23. The package of claim 1, further comprising a thickening agent in an amount of up to about 10% w/w of the composition.

24. The package of claim 1, further comprising a free-radical stabiliser in an amount of up to about 2% w/w of the composition.

25. The package of claim 1, further comprising a colorant and an organic liquid.

26. The package of claim 25, wherein the colorant is present in an amount of from about 20% w/w to about 80% w/w of combined colorant and organic liquid, and, taken together, the colorant and the organic liquid amount to up to 10% w/w of the composition.

27. The package of claim 25, wherein the colorant is a pigment.

28. The package of claim 25, wherein the organic liquid is an oil.

29. The package of claim 28, wherein the oil is selected from the group consisting of: castor oil, dehydrated castor oil, cotton seed oil, fish oil, linseed oil, menhaden oil, oiticaca oil, palm kernel oil, perilla oil, safflower oil, sardine oil, soybean oil and tung oil.

30. The package of claim 1, further comprising up to 2% w/w of a chelator.

31. The package of claim 1, wherein the viscosity of the nail coating composition is from about 500 to about 2000 cPs.

32. A method of applying the nail coating composition of claim 1 to a nail, the method comprising:
(a) contacting the nail with the nail coating composition; and
(b) exposing the nail coating composition to radiation to cure the nail coating composition.

33. The method of claim 32, wherein the nail coating composition is exposed for a period of time of from about 1 minute to about 5 minutes.

34. The method of claim 32, wherein the radiation is sunlight.

35. The method of claim 32, wherein the radiation is radiation generated from a radiation source having a wavelength of from about 200 nm to about 760 nm and an intensity of radiation of from about 0.1 mW/cm$^2$ to about 100 mW/cm$^2$.

36. The method of claim 32 wherein a single coat of the nail coating composition is applied to the nail.

37. A nail coating composition, comprising:
a radiation curable component comprising an acrylate-terminated oligomer in combination with at least one acrylate monomer; wherein the acrylate-terminated oligomer is present in an amount of from about 5% to about 80% w/w of the composition; wherein the acrylate monomer is present in an amount of from about 10% to about 40% w/w of the composition; and
a thiol component comprising a compound containing two or more SH groups, wherein: (i) when the thiol component is a bis functional thiol it is present in an amount of from 15% to about 90% w/w of the nail coating composition; (ii) when the thiol component is a tris functional thiol it is present in an amount of from 15% to about 90% w/w of the nail coating composition; and (iii) when the thiol component is a tetra or higher functional component it is present in an amount of from 5% to about 90% w/w of the nail coating composition.

38. A nail coating composition, comprising:
a radiation curable component comprising: (i) an allyl-terminated oligomer in combination with at least one acrylate monomer and at least one acrylate-terminated oligomer; or (ii) an allyl-terminated oligomer in combination with at least one acrylate monomer; wherein the acrylate-terminated oligomer and/or the allyl-terminated oligomer is present in an amount of from about 5% to about 80% w/w of the composition; wherein the acrylate monomer is present in an amount of from about 10% to about 40% w/w of the composition; and
a thiol component comprising a compound containing two or more SH groups, wherein: (i) when the thiol component is a bis functional thiol it is present in an amount of from 15% to about 90% w/w of the nail coating composition; (ii) when the thiol component is a tris functional thiol it is present in an amount of from 15% to about 90% w/w of the nail coating composition; and (iii) when the thiol component is a tetra or higher functional component it is present in an amount of from 5% to about 90% w/w of the nail coating composition.

39. A nail coating composition, comprising:
a radiation curable component comprising an acrylate-terminated oligomer in combination with at least one acrylate monomer; and
a thiol component comprising a compound containing two or more SH groups, wherein: (i) when the thiol component is a bis functional thiol it is present in an amount of from 15% to about 90% w/w of the nail coating composition; (ii) when the thiol component is a tris functional thiol it is present in an amount of from 15% to about 90% w/w of the nail coating composition; and (iii) when the thiol component is a tetra or higher functional component it is present in an amount of from 5% to about 90% w/w of the nail coating composition.

40. A nail coating composition, comprising:
a radiation curable component comprising: (i) an allyl-terminated oligomer in combination with at least one acrylate monomer and at least one acrylate-terminated oligomer; or (ii) an allyl-terminated oligomer in combination with at least one acrylate monomer; and
a thiol component comprising a compound containing two or more SH groups, wherein: (i) when the thiol component is a bis functional thiol it is present in an amount of from 15% to about 90% w/w of the nail coating composition; (ii) when the thiol component is a tris functional thiol it is present in an amount of from 15% to about 90% w/w of the nail coating composition; and (iii) when the thiol component is a tetra or higher functional component it is present in an amount of from 5% to about 90% w/w of the nail coating composition.

41. The package of claim 1, wherein the thiol component is a tetra or higher functional component, and is present in an amount of from 5% to about 50% w/w.

42. The package of claim 1, wherein the thiol component is a tetra or higher functional component, and is present in an amount of from 5% to about 40% w/w.

43. The package of claim 1, wherein the thiol component is a tetra or higher functional component, and is present in an amount of from 10% to about 30% w/w.

44. The package of claim 1, wherein the thiol component is a bis- and/or tris-functional thiol and is present in an amount of from 15% to 50% w/w.

45. The package of claim 1, wherein the thiol component is a bis- and/or tris-functional thiol and is present in an amount of from 15% to 40% w/w.

* * * * *